United States Patent
Hohjoh et al.

(10) Patent No.: US 10,934,543 B2
(45) Date of Patent: Mar. 2, 2021

(54) INDUCER OF MUSCLE DIFFERENTIATION

(71) Applicant: National Center of Neurology and Psychiatry, Tokyo (JP)

(72) Inventors: Hirohiko Hohjoh, Tokyo (JP); Masashi Fukuoka, Tokyo (JP)

(73) Assignee: NATIONAL CENTER OF NEUROLOGY AND PSYCHIATRY, Tokyo (JP)

( * ) Notice: Subject to any disclaimer, the term of this patent is extended or adjusted under 35 U.S.C. 154(b) by 0 days.

(21) Appl. No.: 16/341,291

(22) PCT Filed: Oct. 13, 2017

(86) PCT No.: PCT/JP2017/037120
§ 371 (c)(1),
(2) Date: Apr. 11, 2019

(87) PCT Pub. No.: WO2018/070510
PCT Pub. Date: Apr. 19, 2018

(65) Prior Publication Data
US 2019/0330627 A1 Oct. 31, 2019

(30) Foreign Application Priority Data
Oct. 13, 2016 (JP) .............. JP2016-201786

(51) Int. Cl.
C12N 15/113 (2010.01)
A61P 21/00 (2006.01)

(52) U.S. Cl.
CPC .......... *C12N 15/113* (2013.01); *A61P 21/00* (2018.01); *C12N 2310/141* (2013.01)

(58) Field of Classification Search
CPC .............. A01K 2207/05; C12N 15/113; C12N 2310/141
See application file for complete search history.

(56) References Cited

U.S. PATENT DOCUMENTS

2003/0195163 A1* 10/2003 Wu .............. A61P 9/00 514/44 A
2010/0292297 A1 11/2010 Wang et al.
2015/0291959 A1 10/2015 Tsai et al.

FOREIGN PATENT DOCUMENTS

| CN | 101954094 A | 1/2011 |
| CN | 105368834 A | 3/2016 |
| EP | 2446929 A1 | 5/2012 |
| EP | 2842581 A1 | 3/2015 |
| JP | 2009519339 A | 5/2009 |

OTHER PUBLICATIONS

Jia et al. Int. J. Mol. Sci. 15, 196-308 (Year: 2014).*
Eulalio et al. Nature 492: 376-384 (Year: 2012).*
Gabisonia et al. Nature 569, 418-422 and supplementary support including methods and tables, pp. 1-20 (Year: 2019).*
Alexander et al. Cell Death and Differiation 20, 1194-1208 (Year: 2013).*
Sandri, "Signaling in Muscle Atrophy and Hypertrophy", Physiology (Bethesda), 2008, vol. 23, pp. 160-170.
Nikawa et al., "Skeletal muscle gene expression in space-flown rats", FASEB Journal, 2004, vol. 18, pp. 522-524 (https://doi.org/10.1096/fj.03-0419fje).
Suzuki et al., "NO production results in suspension-induced muscle atrophy through dislocation of neuronal NOS", Journal of Clinical Investigation, 2007, vol. 117 (9), pp. 2468-2476 (https://doi.org/10.1172/JCI30654).
Altun et al., "Muscle Wasting in Aged, Sarcopenic Rats is Associated with Enhanced Activity of the Ubiquitin Proteasome Pathway", Journal of Biological Chemistry, 2010, vol. 285 (51), pp. 39597-39608.
Dumont et al., "Intrinsic and extrinsic mechanisms regulating satellite cell function", Development, 2015, vol. 142, pp. 1572-1581.
Sandri, "Signaling in Muscle Atrophy and Hypertrophy", Physiology, 2008, vol. 23, pp. 160-170.
Nikawa et al., "Skeletal muscle gene expression in space-flown rats", The FASEB Journal, 2004, vol. 18, pp. 1-24.
Suzuki et al., "NO production results in suspensioninduced muscle atrophy through dislocation of neuronal NOS", The Journal of Clinical Investigation, 2007, vol. 117, No. 9, pp. 2468-2476.
Zhou et al., "Reversal of Cancer Cachexia and Muscle Wasting by ActRIIB Antagonism Leads to Prolonged Survival", Cell, 2010, vol. 142, pp. 531-543
Altun et al., "Muscle Wasting in Aged, Sarcopenic Rats is Associated with Enhanced Activity of the Ubiquitin Proteasome Pathway", The Journal of Biological Chemistry, 2010, vol. 285, No. 51, pp. 39597-39608.
Shimizu et al., "Crosstalk between Glucocorticoid Receptor and Nutritional Sensor mTOR in Skeletal Muscle", Cell Metabolism, 2011, vol. 13, pp. 170-182.
Bartel, "MicroRNAs: Genomics, Biogenesis, Mechanism, and Function", Cell, 2004, vol. 116, pp. 281-297.
Kawamata et al., "Structural determinants of miRNAs for RISC loading and slicer-independent unwinding", nature structural & molecular biology, 2009, vol. 16, No. 9, pp. 953-961.
Park et al., "Carvedilol-responsive microRNAs, miR-199a-3p and -214 protect cardiomyocytes from simulated ischemia-reperfusion injury", Am J Physiol Heart Circ Physiol, 2016, vol. 311, No. 2, pp. H371-H383.

(Continued)

*Primary Examiner* — Brian Whiteman
(74) *Attorney, Agent, or Firm* — Lucas & Mercanti, LLP

(57) ABSTRACT

Provided is an agent developed to be capable of alleviating and suppressing muscle atrophy or muscle mass decrease, even for the elderly and even without requiring exercise, by inducing muscle differentiation. Provided is a composition for treating or preventing disorders or diseases associated with muscle atrophy, or for promoting muscle regeneration, the composition comprising, as an active ingredient, an inducer of muscle differentiation consisting of miR-199 or DNA that contains miR-199 gene encoding the miR-199.

4 Claims, 16 Drawing Sheets
Specification includes a Sequence Listing.

(56) References Cited

OTHER PUBLICATIONS

Pencheva et al., "Convergent multi-miRNA Targeting of ApoE Drives LRP1/LRP8-Dependent Melanoma Metastasis and Angiogenesis", Cell, 2012, vol. 151, No. 5, pp. 1068-1082.

Alemdehy et al., "ICL-induced miR139-3p and miR199a-3p have opposite roles in hematopoietic cell expansion and leukemic transformation", Blood, 2015, vol. 125, No. 25, pp. 3937-3948.

Chen et al., "A miR-199a/miR-214 Self-Regulatory Network via PSMD10, TP53 and DNMT1 in Testicular Germ Cell Tumor", Scientific Reports, 2014, vol. 4, No. 6413, pp. 1-8.

Lee et al., "Twist-1 regulates the miR-199a/214 cluster during development", Nucleic Acids Research, 2009, vol. 37, No. 1, pp. 123-128.

Chen et al., "Nanoparticle delivery of stable miR-199a-5p agomir improves the osteogenesis of human mesenchymal stem cells via the HIFI a pathway", Biomaterials, 2015, vol. 53, pp. 239-250.

Supplementary European Search Report for European Application No. EP 17859510.4 (dated Apr. 6, 2020) (11 Pages).

Zhou et al. "MicroRNA expression profiles of porcine skeletal muscle", Animal Genetics, 2010, vol. 41, pp. 499-508.

Chen et al., "MiRNAs regulates skeletal muscle development via down-regulation of myosin heavy chain", FASEB, J.,2013, vol. 27, No. 1, Supplement 939.12, 1 page.

Fukuoka et al., "Analysis of miRNA in Blood of Young and Old Mice: Young Mouse High-expression miRNA Involving in Differentiation of Muscle", The 38th Annual Meeting of the Molecular Biology Society of Japan , The Joint Meeting of the 88th Annual Meeting of the Molecular Biology Society of Japan, 2015, vol. 6, No. 8, 1 page, English translation 1 page.

\* cited by examiner (ANOVA, Dunnett's test, *: p<0.05)

(Student's *t*-test, *: p<0.05)

A

B

*: P<0.05

Figure 7-1
A
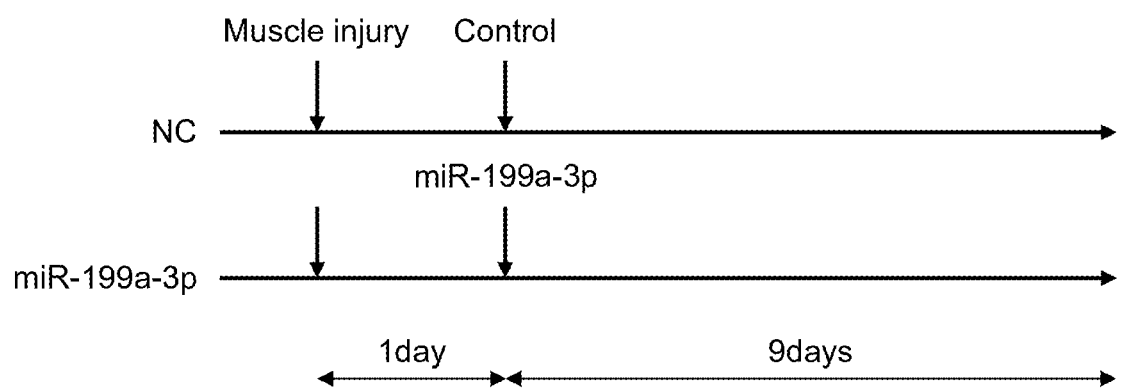
B
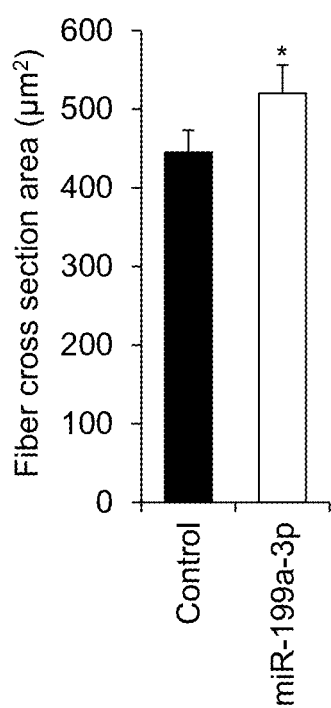
C
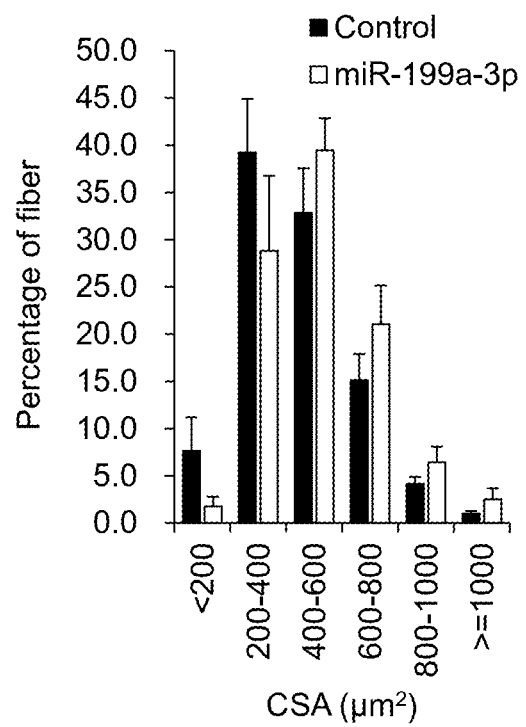
*: P<0.05

D

E

* : P<0.05

*: P<0.05, ***: P<0.001

** : P<0.01

SEQUENCE LISTING

```
<160> NUMBER OF SEQ ID NOS: 26

<210> SEQ ID NO 1
<211> LENGTH: 22
<212> TYPE: RNA
<213> ORGANISM: Homo sapiens
<220> FEATURE:
<223> OTHER INFORMATION: WT hsa-miR-199a-3p

<400> SEQUENCE: 1
acaguagucu gcacauuggu ua                                              22
```

<210> SEQ ID NO 2
<211> LENGTH: 23
<212> TYPE: RNA
<213> ORGANISM: Homo sapiens
<220> FEATURE:
<223> OTHER INFORMATION: WT hsa-miR-199a-5p

<400> SEQUENCE: 2
cccaguguuc agacuaccug uuc                                           23

<210> SEQ ID NO 3
<211> LENGTH: 21
<212> TYPE: RNA
<213> ORGANISM: Ovis aries
<220> FEATURE:
<223> OTHER INFORMATION: WT oar-miR-199a-3p

<400> SEQUENCE: 3
acaguagucu gcacauuggu u                                             21

<210> SEQ ID NO 4
<211> LENGTH: 20
<212> TYPE: RNA
<213> ORGANISM: Gallus gallus
<220> FEATURE:
<223> OTHER INFORMATION: WT gga-miR-199a-3p

<400> SEQUENCE: 4
uacaguaguc ugcacauugg                                               20

<210> SEQ ID NO 5
<211> LENGTH: 22
<212> TYPE: RNA
<213> ORGANISM: Xenopus tropicalis
<220> FEATURE:
<223> OTHER INFORMATION: WT xtr-miR-199a-3p

<400> SEQUENCE: 5
uacaguaguc ugcacauugg uu                                            22

<210> SEQ ID NO 6
<211> LENGTH: 18
<212> TYPE: RNA
<213> ORGANISM: Homo sapiens

<400> SEQUENCE: 6
caguagucug cacauugg                                                 18

<210> SEQ ID NO 7
<211> LENGTH: 76
<212> TYPE: DNA
<213> ORGANISM: Homo sapiens

<400> SEQUENCE: 7
gtacttgggc agtagtgtag agattggttt gcctgttaat gaattcaaac taatctctac   60
actgctgccc aagagc                                                   76

<210> SEQ ID NO 8
<211> LENGTH: 22
<212> TYPE: RNA
<213> ORGANISM: Artificial
<220> FEATURE:
<223> OTHER INFORMATION: miRNA

```
<400> SEQUENCE: 8
acaguagucu gcacauuggu ua                                              22

<210> SEQ ID NO 9
<211> LENGTH: 22
<212> TYPE: RNA
<213> ORGANISM: Artificial
<220> FEATURE:
<223> OTHER INFORMATION: miRNA

<400> SEQUENCE: 9
accaaugugc agacuacuca uu                                              22

<210> SEQ ID NO 10
<211> LENGTH: 21
<212> TYPE: RNA
<213> ORGANISM: Artificial
<220> FEATURE:
<223> OTHER INFORMATION: siRNA

<400> SEQUENCE: 10
uucuccgaac gugucacguu u                                               21

<210> SEQ ID NO 11
<211> LENGTH: 21
<212> TYPE: RNA
<213> ORGANISM: Artificial
<220> FEATURE:
<223> OTHER INFORMATION: siRNA

<400> SEQUENCE: 11
acgugacacg uucggagaau u                                               21

<210> SEQ ID NO 12
<211> LENGTH: 24
<212> TYPE: RNA
<213> ORGANISM: Artificial
<220> FEATURE:
<223> OTHER INFORMATION: siRNA

<400> SEQUENCE: 12
acucguccag gaagaagaga auuu                                            24

<210> SEQ ID NO 13
<211> LENGTH: 25
<212> TYPE: RNA
<213> ORGANISM: Artificial
<220> FEATURE:
<223> OTHER INFORMATION: siRNA

<400> SEQUENCE: 13
uaaauucucu ucuuccugga cgagu                                           25

<210> SEQ ID NO 14
<211> LENGTH: 22
<212> TYPE: RNA
<213> ORGANISM: Artificial
<220> FEATURE:
<223> OTHER INFORMATION: siRNA

<400> SEQUENCE: 14
gagaauuuaa uggaaugauu uu                                              22

<210> SEQ ID NO 15
<211> LENGTH: 22
```

```
<212> TYPE: RNA
<213> ORGANISM: Artificial
<220> FEATURE:
<223> OTHER INFORMATION: siRNA

<400> SEQUENCE: 15
aaucauucca uuaaauucuc uu                                        22

<210> SEQ ID NO 16
<211> LENGTH: 21
<212> TYPE: RNA
<213> ORGANISM: Artificial
<220> FEATURE:
<223> OTHER INFORMATION: siRNA

<400> SEQUENCE: 16
ggauucaucu ccaugauaau u                                         21

<210> SEQ ID NO 17
<211> LENGTH: 21
<212> TYPE: RNA
<213> ORGANISM: Artificial
<220> FEATURE:
<223> OTHER INFORMATION: siRNA

<400> SEQUENCE: 17
uuaucaugga gaugaauccu u                                         21

<210> SEQ ID NO 18
<211> LENGTH: 21
<212> TYPE: RNA
<213> ORGANISM: Artificial
<220> FEATURE:
<223> OTHER INFORMATION: siRNA

<400> SEQUENCE: 18
aggauuuaga agcuugaaau u                                         21

<210> SEQ ID NO 19
<211> LENGTH: 21
<212> TYPE: RNA
<213> ORGANISM: Artificial
<220> FEATURE:
<223> OTHER INFORMATION: siRNA

<400> SEQUENCE: 19
uuucaagcuu cuaaauccuu u                                         21

<210> SEQ ID NO 20
<211> LENGTH: 21
<212> TYPE: RNA
<213> ORGANISM: Artificial
<220> FEATURE:
<223> OTHER INFORMATION: siRNA

<400> SEQUENCE: 20
guggaauuua cauuuaaaau u                                         21

<210> SEQ ID NO 21
<211> LENGTH: 21
<212> TYPE: RNA
<213> ORGANISM: Artificial
<220> FEATURE:
<223> OTHER INFORMATION: siRNA

<400> SEQUENCE: 21
```

```
uuuuaaaugu aaauuccacu u                                            21

<210> SEQ ID NO 22
<211> LENGTH: 21
<212> TYPE: RNA
<213> ORGANISM: Artificial
<220> FEATURE:
<223> OTHER INFORMATION: siRNA

<400> SEQUENCE: 22
gagccagugg aauuuacauu u                                            21

<210> SEQ ID NO 23
<211> LENGTH: 21
<212> TYPE: RNA
<213> ORGANISM: Artificial
<220> FEATURE:
<223> OTHER INFORMATION: siRNA

<400> SEQUENCE: 23
auguaaauuc cacuggcucu u                                            21

<210> SEQ ID NO 24
<211> LENGTH: 22
<212> TYPE: RNA
<213> ORGANISM: Mus musclus
<220> FEATURE:
<223> OTHER INFORMATION: 3'UTR of Lin28b

<400> SEQUENCE: 24
cggccgggau guuaacuacu gc                                           22

<210> SEQ ID NO 25
<211> LENGTH: 22
<212> TYPE: RNA
<213> ORGANISM: Mus musclus
<220> FEATURE:
<223> OTHER INFORMATION: 3'UTR of Lin28b

<400> SEQUENCE: 25
aaggucucuu acuuacuacu ga                                           22

<210> SEQ ID NO 26
<211> LENGTH: 22
<212> TYPE: RNA
<213> ORGANISM: Mus musclus
<220> FEATURE:
<223> OTHER INFORMATION: 3'UTR of Suz12

<400> SEQUENCE: 26
cagaaagugg uuucacuacu gg                                           22
```

INDUCER OF MUSCLE DIFFERENTIATION

CROSS-REFERENCE TO RELATED APPLICATIONS

This application is a 371 of PCT/JP2017/037120, filed Oct. 13, 2017, which claims benefit of Japanese Patent Application No. 2016-201786 filed on Oct. 13, 2016.

TECHNICAL FIELD

The present invention relates to an inducer of muscle differentiation and a composition for treatment or prevention of a disorder or disease associated with muscle atrophy or muscle injury, or for promoting muscle regeneration, comprising the same as an active ingredient.

BACKGROUND ART

In recent years, many of the major developed countries have entered into the era of a super-aging society where the average life-spans of both men and women are more than 80 years. For example, in Japan, the average life-span in 2015 of men was 80.50 years, and that of women was 86.83 years. It is predicted that such an increase in the population of the elderly will continue all over the world for next 20 years or more.

Because many countries are facing a super-aging society, various problems associated with aging have broken to the surface. Examples of such problems include social problems such as restrictions caused by aging to activities of daily living such as walking, a significant QOL decrease caused by such restrictions, the problem of care burden posed by such restrictions to families, and an increase in health care cost. Accordingly, suppression of the decrease of exercise capacity caused by aging and improvement in activities of daily living are important issues for the super-aging society.

The decrease of exercise capacity with age is due to the decrease of skeletal muscle mass and muscle strength caused by a reduction of muscle fiber and muscle atrophy. In general, skeletal muscle mass is regulated by a balance between synthesis mass and degradation mass of protein (Non-Patent Literature 1). For example, a muscle inactive state such as immovable dressing with a cast due to bone fracture or bed resting suppresses protein synthesis and promotes protein degradation, and accordingly decreases the amount of the muscle protein, and as a result, the skeletal muscle mass is reduced and the muscle becomes atrophic. Disuse muscle atrophy caused by such a long-term non-use of muscle may also be caused by not only aging but also space flight under microgravity (Non-Patent Literature 2), muscle immobilization due to tail suspension (Non-Patent Literature 3) and the like, cachexia (Non-Patent Literature 4), sarcopenia (Non-Patent Literature 5), administration of steroid (Non-Patent Literature 6), and the like.

Methods for alleviating or improving reduction of muscle fiber and muscle atrophy for the elderly are extremely important as a solution of the problem, and development of such methods is imperative. In addition, a capability to regulate the induction of muscle differentiation is expected to serve for effective treatment methods against myogenic diseases associated with muscle atrophy and muscle injury, such as muscular dystrophy.

In general, there is a method for treating muscle atrophy, wherein suitable resistance is loaded onto muscle cells using an exercise therapy, whereby protein synthesis is activated to induce muscle hypertrophy. A good example thereof is muscular training. However, in the case of the treatment methods involving exercise, the practice of such a method is difficult in itself for bedridden elderly people and patients with a myogenic disease associated with severe muscle atrophy. In addition, in the elderly, potency of a muscle differentiation decreases by aging, and accordingly, relying on an exercise therapy alone is not promising for suppressing muscle atrophy and increasing skeletal muscle mass. Accordingly, there is a demand for a treatment method wherein, without loading excessive resistance to muscle cells, muscle differentiation can be induced using a drug so that even the elderly can alleviate or suppress muscle atrophy.

CITATION LIST

Non-Patent Literature

Non-Patent Literature 1: Sandri, M., Physiology (Bethesda), 2008, 23: 160-170
Non-Patent Literature 2: Nikawa, T. et al., 2004, FASEB J, 18: 522-524
Non-Patent Literature 3: Suzuki, N. et al., 2007, J Clin Invest, 117: 2468-2476
Non-Patent Literature 4: Zhou, X. et al., 2010, Cell, 142: 531-543
Non-Patent Literature 5: Altun, M. et al., 2010, J Biol Chem, 285: 39597-39608
Non-Patent Literature 6: Shimizu, N. et al., 2011, Cell Metab, 13: 170-182

SUMMARY OF INVENTION

Technical Problem

The present invention is to develop and provide an agent with which muscle differentiation can be induced without loading excessive resistance to muscle cells so that even the elderly and patients with a myogenic disease can alleviate or suppress the decrease of muscle mass or muscle strength due to muscle atrophy or muscle injury.

Solution to Problem

In a process of comprehensive analysis of miRNA in the blood of mice, the present inventors have obtained miR-199a-3p as a miRNA that is highly expressed in young mice and low expressed in old mice. An examination of the effect of miR-199a-3p on muscle differentiation has revealed that miR-199a-3p has a strong muscle differentiation activity. The examination has also proved that the expression of miR-199 raises the expression of miR-1, which is known to express muscle-specifically. Furthermore, administration of miR-199 to mice whose muscle is injured has significantly increased the cross-sectional area of muscle fibers, compared with a control, and promoted muscle regeneration. This effect was the same with the old mice. Although miR-199 is known to express transiently in the telencephalon and the like in the early development, the function of miR-199 in muscle cells has been little reported up to now. This time, however, the present inventors' study has suggested that miR-199 is a master factor that regulates induction of muscle differentiation most upstream, with LIN28B and Suz12 as target genes. In addition, administration of miR-199 has demonstrated recovery of muscle strength in muscular dystrophy model mice and suggested improvement on muscle cells. The present invention is based on these new findings and provides the following.

(1) An inducer of muscle differentiation consisting of miR-199 or a DNA comprising a miR-199 gene encoding the miR-199.

(2) The inducer of muscle differentiation according to (1), wherein the miR-199 is miR-199-3p.

(3) The inducer of muscle differentiation according to (1) or (2), wherein the miR-199 is miR-199a.

(4) The inducer of muscle differentiation according to (3), wherein the miR-199 consists of a base sequence shown in the following (A) to (C):

(a) a base sequence shown in SEQ ID NO: 1;
(b) a base sequence comprising a base sequence derived from the base sequence shown in SEQ ID NO: 1 by the deletion, substitution, or addition of one or three bases; and
(c) a base sequence having a base identity of 85% or more to the base sequence shown in SEQ ID NO: 1.

(5) The inducer of muscle differentiation according to any one of (1) to (4), wherein the miR-199 gene is contained in an expression vector in an expressible state.

(6) A composition for treatment or prevention of a disorder or a disease associated with muscle atrophy or muscle injury, comprising, as an active ingredient, the inducer of muscle differentiation according to any one of (1) to (5).

(7) The composition for treatment or prevention according to (6), wherein the disease associated with muscle atrophy or muscle injury is a myogenic disease.

(8) The composition for treatment or prevention according to (7), wherein the myogenic disease is a muscular dystrophy.

(9) A composition for promoting muscle regeneration, the composition comprising, as an active ingredient, the inducer of muscle differentiation according to any one of (1) to (5).

The present description encompasses the disclosure of Japanese Patent Application No. 2016-201786, which is the basis for the priority of the present application.

Advantageous Effects of Invention

A composition that contains as an active ingredient the inducer of muscle differentiation according to the present invention and that is used for treatment or prevention of a disorder or a disease associated with muscle atrophy or used for promoting muscle regeneration can suppress the progress of muscle atrophy and augment muscle strength or recover muscle strength without loading resistance to muscle cells in a disorder and a disease associated with muscle atrophy and muscle strength decrease and in promoting muscle regeneration at sites of muscle injury. The composition can also serve as a treatment agent or preventive agent useful against muscle atrophy and muscle strength decrease to the elderly for whom an exercise therapy such as rehabilitation is difficult.

BRIEF DESCRIPTION OF THE DRAWINGS

FIG. 2-1 is a diagram showing the expression levels of the muscle-differentiation-related miRNA (miR-1) in C2C12 cells after introducing miR-199a-3p. This diagram shows the relative values obtained assuming that the expression level in the negative control (Neg) without introducing miR-199a-3p is 1. The sign, 199s, represents a MISSION miRNA mimic, HMI0338, that is a commercially available miR-199a-3p, and 199#4 represents miR-199a-3p#4 that is a modified miR-199a-3p prepared in the Examples.

FIG. 2-2 shows the relative values of the expression levels of various miRNAs (miR-1, miR-133a, miR-26a, let-7g, and miR-214) in C2C12 cells introducing 199s, compared with the negative control.

FIG. 3-1 (A-C) is a diagram showing a base sequence alignment between miR-199a-3p and each of the Lin28b gene and the Suz12 gene which are target candidate genes of miR-199a-3p. In Panel A, the upper sequence is a nucleotide sequence shown in SEQ ID NO: 24 corresponding to position 81 to position 102 of the Lin 28b gene. In Panel B, the upper sequence is a nucleotide sequence shown in SEQ ID NO: 25 corresponding to position 983 to position 1004 of the Lin 28b gene. In Panel C, the upper sequence is a nucleotide sequence shown in SEQ ID NO: 26 corresponding to position 973 to position 994 of the Suz12 gene. In Panels A-C, the lower sequence in each Panel is a nucleotide sequence of mouse wild-type miR-199a-3p, shown in SEQ ID NO: 1, which is identical to that of human wild-type miR-199a-3. As shown in FIG. 3-1, Mouse miR-199a-3p has, as candidate target sites, two parts, one from positions 81 to 102 shown in "A" and the other from positions 983 to 1004 shown in "B", on the Lin28b gene, and one part from positions 973 to 994 on the Suz12 gene shown in "C".

FIG. 3-2 is a Western blot diagram showing the expression suppression of the Lin28b gene and Suz12 gene in C2C12 cells when miR-199a-3p was introduced into the cells.

FIG. 4-1 is a diagram showing the expression levels of the Myh1 gene and myogenin (Myog) gene in the presence of siRNA (siSuz12#1 and siSuz12#2) against Suz12.

FIG. 4-2 is a diagram showing the expression levels of the muscular type creatine kinase (Ckm) gene and Myh1 gene in the presence of siRNA (siLin28#3) against Lin28b.

FIG. 5-2 "C" shows the expression level of Ckm in the presence of siLin28b.

FIG. 7-1 (A-C) is a diagram showing the in vivo promotion activity of muscle regeneration involving miR-199a-3p. "A" shows the experiment schedule of Example 7, and "B" and "C" show the results of muscle regeneration in eight-week-old C57/BL6J mice.

FIG. 7-2 is a diagram showing the results of the in vivo promotion activity of muscle regeneration involving miR-199a-3p. "D" and "E" show the results of the muscle regeneration in two-year-old ICR mice.

DESCRIPTION OF EMBODIMENTS

1. Inducer of Muscle Differentiation

1-1. Summary

Figure 1:
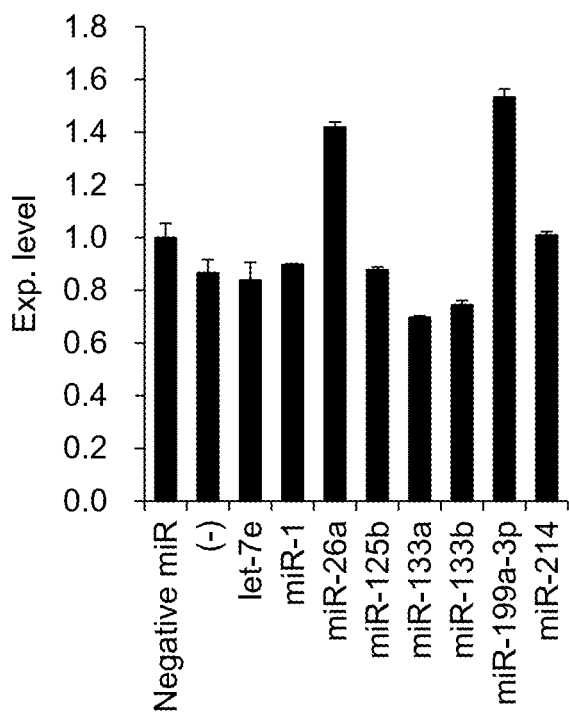
FIG. 1 (A-B) is a diagram showing various miRNAs (let-7e, miR-1, miR-26a, miR-125b, miR-133a, miR-133b, and miR-214) and the induction of muscle differentiation activity that miR-199a-3p constituting the inducer of muscle differentiation according to the present invention has for mouse myoblast line C2C12 cells. This diagram verifies the induction activity of muscle differentiation in terms of the expression levels of myogenin (A) and Myh1 (B) that are muscle differentiation marker proteins.
Figure 1:
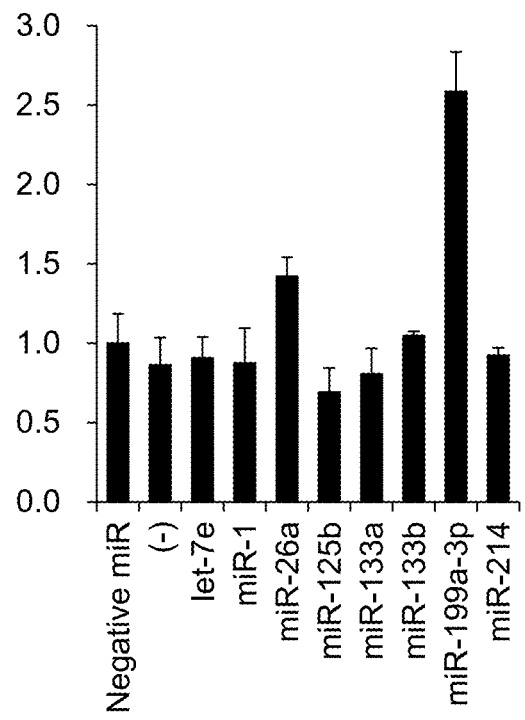

A first aspect of the present invention is an inducer of muscle differentiation. The inducer of muscle differentiation according to the present invention is constituted by a nucleic acid molecule consisting of miR-199, which is one of the miRNAs expressed in vivo, or consisting of a DNA comprising a miR-199 gene encoding the miR-199. The inducer of muscle differentiation according to the present invention serves, in a composition for the induction of muscle differentiation, as an active ingredient of a composition for promoting muscle regeneration or for treatment or prevention of a disorder or a disease associated with muscle atrophy, as described in the below-mentioned second or third aspect.

1-2. Definition of Terms

The terms frequently used herein will be defined as follows.

As used herein, the term "muscle differentiation" refers to differentiation of myoblasts into muscle cells. The term "muscle cells" refers to skeletal-muscle-constituting cells, in other words, muscle fibers.

As used herein, the term "inducer of muscle differentiation" refers to an agent that acts on and induces myoblasts to differentiate into muscle cells and increases muscle cells. The term "increase in muscle cells" refers to any one of promotion of muscle hypertrophy, suppression of muscle atrophy, an increase in muscle strength, and maintenance of muscle strength, or a combination thereof.

As used herein, the term "muscle hypertrophy" refers to an increase of muscle weight due to an increase of single muscle fiber weight or an increase of cross-sectional area accompanying an increase in the amount of endogenous protein, and the term "promotion of muscle hypertrophy" refers to promoting an increase of muscle weight due to an increase of muscle fiber weight or an increase of cross-sectional area by promoting an increase in the amount of endogenous protein in single muscle fibers. The term "muscle atrophy" means a state in which a single muscle fiber weight or cross-sectional area is partially reduced, accompanied by a muscle strength decrease, and the term "alleviation of muscle atrophy" refers to inhibiting a single muscle fiber weight reduction or cross-sectional area reduction, or to slowing the reduction speed, or to increasing the single muscle fiber weight or cross-sectional area which has been reduced. The term "muscle strength" refers to a force that shrinks muscle (muscle tension), and the term "increase or maintenance of muscle strength" refers to an increase in or maintenance of the force.

The term "miRNA (microRNA)" refers to a single-stranded noncoding RNA having a length of 21 to 23 bases, present in cells. miRNA is generated by transcription from the genome to a pre-precursor state called pri-miRNA, followed by processing the pri-miRNA into a precursor called pre-miRNA by an endonuclease called Drosha in the nucleus. Further, the pre-miRNA is processed by an endonuclease called Dicer outside the nucleus and formed into an intermediate double-stranded miRNA (miRNA/miRNA*) consisting of miRNA and miRNA* (miRNA star). The miRNA/miRNA* is taken into RISC (RNA-induced silencing complex) which is a protein complex, and finally, the miRNA which is one of the RNA strands functions as a mature miRNA (mature miRNA) (Bartel D P, 2004, Cell, 116:281-297, Kawamata T., et al., 2009, Nat Struct Mol Biol., 16(9):953-960). It is known that mature miRNA binds to mRNA for the target gene in RISC and inhibits the translation thereof to regulate the expression of the target gene in a suppressive manner. Accordingly, pri-miRNA and pre-miRNA as a precursor, and mature miRNA usually exist in cells. Herein, miRNA is a concept encompassing both a miRNA precursor and a mature miRNA, but means a mature miRNA unless otherwise specified.

It has conventionally been thought that miRNA star strands are degraded easily and that miRNA strands function as mature miRNAs, but it has been revealed that many miRNA star strands having functionality exist, and accordingly, the wording, miRNA/miRNA*, has come to be replaced with miRNA-5p/miRNA-3p which means the 5' side and 3' side positions in the hairpin structure of pre-miRNA. In view of this, the wording is used in the same manner also herein.

1-3. Constitution

The inducer of muscle differentiation according to the present aspect is constituted by a nucleic acid molecule consisting of miR-199, or consisting of a DNA comprising a miR-199 gene encoding the miR-199.

"miR-199" is one of the vertebrate-specific miRNAs, and is known to be involved in the onset and progression of various cancers, protection of cardiomyocytes, or various cell mechanisms and developmental mechanisms such as skeletogenesis (Park K M, et al., 2016, Am J Physiol Heart Circ Physiol, 311(2):H371-383; Pencheva N., et al., 2012, Cell, 151(5): 1068-1082; Alemdehy M. F., et al., 2015, Blood, 25(25):3937-3948; Chen B. F., et al., 2014, Sci Rep, 4:6413). With regard to miR-199 in muscle, it has been known that the expression of miR-199 transiently increases in the early development, and then the miR-199 disappears rapidly (Lee Y. B., et al., 2009, Nucleic Acids Res. 37(1): 123-128). However, there has been no report on the relation to muscle differentiation and diseases such as myogenic disease, and the specific functions have been unknown.

Like many other miRNAs, miR-199 such as the above-mentioned miR-199-5p and miR-199-3p also exists. It is known that, among these, miR-199-3p is expressed mainly in the hindbrain, and miR-199-5p is expressed mainly in the limb bud (Lee Y. B., et al., 2009, Nucleic Acids Res. 37(1):123-128). The miR-199 constituting the inducer of muscle differentiation according to the present invention may be either miR-199-5p or miR-199-3p, and is preferably miR-199-3p whose main expression sites are muscle tissues.

In addition, miR-199 paralogs such as miR-199a and miR-199b in the same organism species are known. The miR-199 constituting the inducer of muscle differentiation according to the present invention may be either paralog.

The miR-199 constituting the inducer of muscle differentiation according to the present invention encompasses a wild-type miR-199 or a mutant miR-199 having a same activity or more than a wild-type miR-199.

Examples of wild-type miR-199 include a human wild-type miR-199 such as a human wild-type mature miR-199a-3p (hsa-miR-199a-3p) or a human wild-type mature miR-199b-3p (hsa-miR-199b-3p) having the base sequence shown in SEQ ID NO:1, and human wild-type mature miR-199a-5p (hsa-miR-199a-5p) having the base sequence shown in SEQ ID NO:2. Furthermore, such examples also include wild-type miR-199 orthologs derived from other organism species and having the same activity as human wild-type miR-199. In general, it is known that miR-199 is preserved extremely highly among organism species, and most of the wild-type miR-199 orthologs in mammals in particular have a base identity of 100% to human wild-type miR-199 or the same identity except for the deletion or substitution of one base. For example, the wild-type mature miR-199a-3p of *Mus musclus, Equus caballus, Sus scrofa,* and *Bos taurus* has a base identity of 100% to human wild-type mature miR-199a-3p. In addition, the wild-type mature miR-199a-3p of *Ovis aries* and *Capra hircus* has the same base sequence as human wild-type mature miR-199a-3p except for the deletion of one base from the 3' end, as shown in SEQ ID NO:3. Furthermore, even others than mammals have an extremely high base identity to human wild-type miR-199. For example, *Gallus* wild-type miR-199-3p of SEQ ID NO:4 has a base identity of 86% to human wild-type miR-199a-3p, *Xenopus tropicalis* wild-type miR-199a-3p of SEQ ID NO:5 has a base identity of 95% to human wild-type miR-199a-3p, *Salmo salar, Cyprinus carpio,* and *Ictalurus punctatus* have a base identity of 100% to *Capra hircus* or *Ovis aries* wild-type miR-199a-3p, and *Danio rerio* has a base identity of 100% to *Xenopus tropicalis* wild-type miR-199a-3p. As obvious from the base sequences exemplified above, the base sequence shown in SEQ ID NO: 6 is an active region of miR-199 and the same no matter what the species may be. It is considered that, owing to the high interspecific sequence identity, the miR-199 activities of organism species are compatible, and use of the miR-199 of any organism species exhibits the same activity and the same effect.

Examples of mutant miR-199 includes: RNA comprising a base sequence derived from the base sequence or wild-type miR-199 by the deletion, substitution, or addition of one or three bases; RNA having a base sequence having a base identity of 85% or more, 90% or more, or 95% or more to the base sequence shown in wild-type miR-199; and RNA having a base sequence that hybridizes, under high stringent conditions, with a nucleic acid fragment having a base sequence complementary to all or part of the base sequence shown in wild-type miR-199. As used herein, the term "base identity" refers to a ratio (%), wherein the base sequence shown in wild-type miRNA-199 and that of mutant miR-199 are aligned, and a gap is introduced into one of the base sequences, if necessary, so that the degree of coincidence between both bases can be the highest, and wherein the ratio is a ratio of the number of the same bases of one miRNA as the other miRNA to the total number of the bases of the other miRNA. A % identity can be easily calculated using a known program such as a homology search program, BLAST search (Basic local alignment search tool; Altschul, S. F. et al, J. Mol. Biol., 215, 403-410, 1990). In addition, as used herein, the term "high stringent conditions" refer to conditions of high temperature and low salt concentration such that no nonspecific hybrid is formed. For example, in washing carried out after hybridization, the conditions are based on 1×SSC or less at 60° C. to 68° C., preferably 0.1×SSC or less at 65° C. to 70° C.

The term "miR-199 gene" is a gene encoding the miR-199. The miR-199 gene is corresponding to a DNA comprising a polynucleotide having the base sequence substituted uracil (U) in the base sequence of the miR-199 with thymine (T), for example, a gene encoding a miR-199 precursor such as a pre-miRNA of miR-199 (pre-miR-199). Specific examples include a human wild-type pre-miR-199a having the base sequence shown in SEQ ID NO:7.

The miR-199 gene is preferably contained in an expression vector in an expressible state.

The term "expression vector" refers to an expression unit capable of regulating the expression of a gene or gene fragment of interest contained in the vector. The term "in an expressible state" refers to a state in which a gene or the like of interest can be transcribed in a host cell under predetermined conditions. Specifically, a state corresponds to the state placing a gene or the like of interest under the regulation of a promoter. When the promoter is activated, the expression of the gene or the like of interest under the regulation is induced. As expression vectors, various expression vectors capable of replicating and expressing in a host cell can be utilized. Examples include virus vectors, plasmid vectors, and the like. Examples of virus vectors include various vectors derived from retroviruses (including lentiviruses), adenoviruses, adeno-associated viruses, Sendai viruses, and the like. As these expression vectors, products commercially available from manufacturers can be used. However, miR-199 can function as a master factor in muscle differentiation, and accordingly, may cause not only muscle differentiation but also a serious side effect to organisms when overexpressed constantly. Accordingly, when an inducer of muscle differentiation consisting of a miR-199 gene or an expression vector comprising a miR-199 gene in an expressible state is administered to an organism, the miR-199 gene is preferably ready to be expressed transiently. Examples of such methods include using, as a promoter contained in an expression vector, an expression inducible promoter capable of regulating the expression timing in a cell.

2. Composition for Treatment or Prevention of Disorder or Disease Associated with Muscle Atrophy or Muscle Injury 2-1. Summary A second aspect of the present invention relates to a composition for treatment or prevention of a disorder or a disease associated with muscle atrophy or muscle injury (hereinafter simply referred to as a "composition for treatment or prevention"). An inducer of muscle differentiation constituted by a nucleic acid molecule according to the first aspect can be used as a composition comprising the agent. The composition for treatment or prevention according to the present invention is a composition that contains, as an active ingredient, an inducer of muscle differentiation according to the first aspect, and that is administered to a test subject who has or may have in the future a disorder or a disease associated with muscle atrophy or muscle injury, to thereby treat or prevent the disorder or disease.

2-2. Constitution

The composition for treatment or prevention according to the present invention contains an active ingredient and a carrier as constituent ingredients. Below, the constituent ingredients will each be described.

2-2-1. Active Ingredient

The composition for treatment or prevention according to the present aspect contains, as an active ingredient, an inducer of muscle differentiation according to the first aspect. The composition for treatment or prevention according to the present invention can contains one or more inducer of muscle differentiations according to the first aspect. For example, the composition may contain, as active ingredients, two kinds of inducer of muscle differentiations: human wild-type miR-199a-3p and human mutant miR-199a-3p. In addition, the composition can be combined with (an)other known inducer of muscle differentiation(s) that is/are known to induce muscle differentiation, for example, miR-1, miR133a, miR-26a, miR-214, and the like.

The amount (content) of the inducer of muscle differentiation according to the first aspect contained in the composition for treatment or prevention varies depending on the kind and/or active amount (dosage or intake) of the inducer of muscle differentiation contained in the composition for treatment or prevention, the kind of the disorder or disease, the dosage form of the composition for treatment or prevention, and the kind of the below-mentioned carrier or additive. Therefore, it can be suitably determined taking the conditions into account. As used herein, the term "active amount" refers to an amount that is necessary for the inducer of muscle differentiation to achieve the function expected from the active ingredient in the composition for treatment or prevention and that causes little or no harmful action to an organism to whom the composition is applied. The active amount can vary depending on the various conditions such as the test subject information, the route of administration, and the frequency of administration, and the like. As used herein, the term "test subject" refers to an organism serving as a subject to whom the composition for treatment or prevention, the inducer of muscle differentiation, or the composition for promoting muscle regeneration according to the present invention is applied. Applicable examples thereof include human, domestic animals (crummy, horse, sheep, goat, pig, chicken, ostrich and the like), race horses, pet animals (dog, cat, rabbit, and the like), laboratory animals (mouse, rat, guinea pig, monkey and the like), and the like. Preferably examples of test subjects are humans, domestic animals, and race horses. In addition, the term "test subject information" refers to various kinds of information on individual organisms to whom the composition for treatment or prevention is applied. The information includes, for example, the health status of the whole body, the kind and severity of another disease and/or illness if the test subject may be affected, the age, body weight, gender, dietary habit, drug sensitivity, taking of a combined drug, resistance to treatment, and the like. The final effective amount of the inducer of muscle differentiation and the dose calculated on the basis of the final effective amount are determined finally on the judgement of a doctor, veterinarian, or the like in accordance with the information and the like on each individual test subject. Thus, the amount of the inducer of muscle differentiation contained in the composition for treatment or prevention according to the present invention varies depending on the conditions. In a case where a high dose of the composition for treatment or prevention is necessary to obtain the pharmacological effect of the inducer of muscle differentiation, the composition can be administered in some installments in order to alleviate the burden on a test subject. For example, the usual effective amount of the inducer of muscle differentiation per day per adult may be administered once or a few times per day over a few days to one week, one month, a few months, half a year, or one year.

2-2-2. Carrier

The composition for treatment or prevention according to the present invention contains a pharmaceutically acceptable carrier. The term "pharmaceutically acceptable carrier" refers to an additive agent usually used in the art of formulation. Examples thereof include solvents and excipients.

The solvent may be, for example, any one of water, a pharmaceutically acceptable aqueous solution other than water, and a pharmaceutically acceptable organic solvent. Examples of aqueous solutions include buffers, physiological saline, and isotonic solutions comprising dextrose or other adjuvants. The buffers are used to maintenance the pH in a solution comprising a skeletal muscle precursor cell as the active ingredient. Specific examples include PBS, HEPES, MOPS, Tricine, and the like. With regard to solvents such as buffers, the description in Green, M. R. and Sambrook, J., 2012, Molecular Cloning: A Laboratory Manual Fourth Ed., Cold Spring Harbor Laboratory Press, Cold Spring Harbor, N.Y., may be referred to.

Those which apply to the adjuvants are, for example, D-sorbitol, D-mannose, D-mannitol, sodium chloride, and in addition, low concentration nonionic surfactants, polyoxyethylene sorbitan fatty acid esters, and the like. Examples of organic solvents include ethanol.

Excipients are mainly used to facilitate the formation of a dosage form and to maintain the dosage form and pharmacological effect of an inducer of muscle differentiation that is an active ingredient. Excipients are used if necessary. An excipient may suitably contain a binder, disintegrator, filler, emulsifier, fluid addition regulating agent, lubricant, solubilizer, suspension, diluent, dispersing agent, surfactant, soothing agent, stabilizer, absorbefacient, expander, humectant, adsorbent, preservative, antioxidant, buffering agent, isotonizing agent, human serum albumin, or the like.

Specific examples of binders include starch paste made with vegetable starch, pectin, xanthan gum, simple syrup, glucose liquid, gelatin, tragacanth, methylcellulose, hydroxypropylmethylcellulose, sodium carboxymethylcellulose, shellac, paraffin, polyvinyl pyrrolidone, and combinations thereof.

Examples of disintegrators include the starches, lactose, carboxymethyl starches, cross-linked polyvinyl pyrrolidone, agar, laminaran powders, sodium bicarbonate, calcium carbonate, alginic acids or sodium alginate, polyoxyethylene sorbitan fatty acid esters, sodium lauryl sulfate, monoglyceride stearate, or salts thereof.

Examples of fillers include vaseline, the sugars, and/or calcium phosphate.

Examples of emulsifiers include sorbitan fatty acid esters, glycerin fatty acid esters, sucrose fatty acid esters, and propylene glycol fatty acid esters.

2-3. Dosage Form and Mode of Administration

The dosage form of the composition for treatment or prevention according to the present invention varies depending on the mode of administration and/or formulations. However, it is not limited as long as the dosage form can achieve the pharmacological effect in vivo after administration without inactivating the inducer of muscle differentiation according to the first aspect as an active ingredient or other additional active ingredients by degradation or the like.

In general, modes of administration can be broadly classified into oral administration and parenteral administration. The composition for treatment or prevention according to the present invention may be administered by either mode. The parenteral administration is preferable because the inducer of muscle differentiation that is an active ingredient is constituted by a nucleic acid, i.e. RNA or DNA. Accordingly, the composition for treatment or prevention can be made into a dosage form suitable for each mode of administration.

Parenteral administration is further subclassified into systemic administration, interstitial administration, transepidermal administration, transmucosal administration, and transrectal administration. The composition for treatment or prevention according to the present invention functions in myoblasts and muscle cells by nature, and accordingly, systemic administration via the cardiovascular system is preferable such as local administration into muscle tissues, intravascular administration, or intralymphatic administration. Direct local administration into muscle tissues is preferable. For dosage forms suitable for the systemic or interstitial administration, liquid formulations such as injection solutions are preferable. For example, injection solutions are formulated in combination with excipients such as an emulsifier, suspension, surfactant, stabilizer, and pH regulator, if appropriate, and by mixing in the form of a unit dose required by a generally acceptable pharmaceutical manufacturing practice, and are provided in the state of a unit dose ampoule or high dose container.

Intravascular administration such as intravenous injection is convenient because it is possible to systemically deliver, via bloodstreams, to the inducer of muscle differentiation that is an active ingredient in the composition for treatment or prevention according to the present invention. However, it is preferable to contrive such that the inducer of muscle differentiation comprising a nucleic acid as a constituent ingredient is delivered, without being degraded by nuclease in the blood, to muscle tissues having myoblasts and muscle cells that are target cells. For example, allowing a DNA comprising miR-199 or a miR-199 gene to be taken in adeno-associated virus (AAV) vector particles makes it possible that the agent eludes degradation by nuclease in the blood and is delivered to muscle tissues of interest.

In the case of introducing the composition for treatment or prevention according to the present invention into muscle tissues by transepidermal administration or transmucosal administration, examples of dosage forms suitable for the modes of administration include liquid formulations (including liniments, eyedrops, nasal drops, and inhalants), suspensions (including emulsions and creams), powders (including nasal drops and inhalants), pastes, gels, ointments, plasters, and the like.

In the case of being administered by oral administration, the composition for treatment or prevention according to the present invention can be in a dosage form such as a solid formulation (including a tablet, pill, sublingual agent, capsule, drop, and troche), granule, powder, microgranule, liquid formulation (including a peroral liquid formulation, suspension, emulsion, and syrup), or the like. If required, solid formulations can be made in a dosage form having a coating known in the art, for example, a sugar coated tablet, gelatin protective tablet, enteric-coated tablet, film-coated tablet, double lock, or multilayer tablet.

Since the composition for treatment or prevention according to the present aspect is applied for treatment or prevention of a disorder or a disease associated with muscle atrophy or for promoting muscle regeneration at muscle injury sites, the applicable sites are the skeletal muscle in principle.

2-4. Intended Disorder and Disease

Disorders or diseases intended for the treatment or prevention of the composition for treatment or prevention according to the present aspect are disorders or diseases associated with muscle atrophy or muscle injury and muscle strength decrease. As used herein, the term "treatment" refers to alleviation or healing of disorders or contracted diseases and/or symptoms associated with the disorders or diseases. As used herein, the term "prevention" refers to forestalling the onset of a disorder or the contraction of a disease.

Examples of disorders associated with muscle atrophy include: disuse muscle atrophy caused by a muscle inaction state such as immovable dressing with a cast, bed resting, or the like; malignancy; cachexia associated with a chronic disease such as of a respiratory tract; aging (sarcopenia); side effects caused by administration of a steroid; and muscle atrophy under microgravity such as in a life or the like in aerospace.

In addition, examples of diseases associated with muscle atrophy or muscle injury and muscle strength decrease include myogenic diseases presenting a muscle symptom, such as muscle strength decrease, owing to an abnormality generated in the skeletal muscle. The examples do not include muscle injury due to a physical factor such as muscle rupture. Myogenic diseases can be broadly classified into inflammatory muscle diseases and non-inflammatory muscle diseases according to etiology.

An "inflammatory muscle disease" is an autoimmune inflammatory muscle disease and is accompanied by a muscle strength decrease in extremities muscle, trunk muscle, neck muscle, pharyngeal muscle, and the like. Specific examples of inflammatory muscle diseases include polymyositis (PM), dermatomyositis (DM), inclusion body myositis (IBM), anti-synthetase syndrome (ASS), and immune-mediated necrotizing myopathy (iNM).

"Non-inflammatory muscle diseases" are non-autoimmune inflammatory muscle diseases, and most of the diseases are hereditary muscle diseases (genetic muscle diseases (hMD): hereditary/genetic muscle diseases) caused by genetic variation. Specific examples of non-inflammatory muscle diseases include muscular dystrophies (including various muscular dystrophies such as Duchenne, Becker, Emery-Dreifuss, limb-girdle, facioscapulohumeral, oculopharyngeal, and hereditary ones), myopathies (including hereditary, distal, hypothyroid, and steroid ones, and the like), amyotrophic lateral sclerosis, Danon disease, myasthenic syndrome, mitochondrial disease, myoglobinuria, glycogen storage disease, periodic paralysis, and the like.

3. Composition for Promoting Muscle Regeneration 3-1. Summary

A third aspect of the present invention relates to a composition for promoting muscle regeneration. The inducer of muscle differentiation according to the first aspect can be used not only for the composition for treatment or prevention according to the second aspect, but also for various other compositions depending on the use. The composition for promoting muscle regeneration according to the present invention contains, as an active ingredient, the inducer of muscle differentiation according to the first aspect, and is used in an application other than the treatment or prevention of a disorder or a disease associated with muscle atrophy in the second aspect, for example, used as a composition for promoting regeneration of the skeletal muscle injured by a physical factor such as muscle rupture.

As used herein, the term "skeletal muscle injury" refers to necrosis of a skeletal muscle cell by the cell membrane fragility or a physical defect in a skeletal muscle cell. Necrosis of a cell is a phenomenon recognized in muscle cells and the like in myogenic diseases, but here means a phenomenon that occurs in muscle cells exposed to a physical stimulus due to a hurt or exercise resistance.

3-2. Constitution, Dosage Form, and Mode of Administration

The basic constitution of the composition for promoting muscle regeneration according to the present invention conforms to the composition for treatment or prevention according to the second aspect. In other words, the composition for treatment or prevention according to the second aspect is applied to a test subject having a disorder or a disease associated with muscle atrophy, whereas the composition for promoting muscle regeneration according to the present invention is applied to a test subject whose skeletal muscle is injured by a wound or a test subject whose skeletal muscle is reduced through aging, debility, or the like. That is, the composition for promoting muscle regeneration differs from the composition for treatment or prevention according to the third aspect only in application. Accordingly, a specific description related to the constitution, dosage form, and mode of administration corresponding to those of the third aspect is omitted.

3-3. Applicable Subject

The agent for promoting the skeletal muscle regeneration according to the present invention can promote muscle differentiation from myoblasts into muscle cells, thereby supplement or fill the skeletal muscle of injured sites, and recover the muscle amount to the original level, when part of the skeletal muscle is injured by a physical resistance due to excessive exercise or by a wound or when a muscle cell reduction or muscle atrophy increases through aging. Accordingly, the applicable subjects are test subjects whose skeletal muscle is partially injured owing to an accident, surgery, or the like, and test subjects whose skeletal muscle is reduced through aging.

EXAMPLES

Below, the present invention will be described with reference to specific examples. However, the following Examples are only illustrations of the present invention, and each condition in the present invention is not limited to any condition or the like described in Examples. The basic experimental approaches in each Example are based on the methods described in Green, M. R. and Sambrook, J., 2012 (supra).

<Materials and Methods>

The experimental materials and experimental methods used in the below-mentioned Examples will be described.

1. Cultured Cell Line and Cell Culture

As cultured cell lines, mouse myoblast line C2C12 cells, mouse primary myoblasts, and human skeletal muscle satellite cells were used.

C2C12 cells (RIKEN Cell Bank) were cultured in 5% $CO_2$ at 37° C. using a Dulbecco's modified Eagle's medium (DMEM) (Wako Pure Chemical Industries, Ltd.) containing 10% fetal bovine serum (FBS; Thermo Fisher Scientific K.K.) and 1% penicillin/streptomycin (Wako Pure Chemical Industries, Ltd.). Differentiation of C2C12 cells into myotube cells was induced by culture in 5% $CO_2$ at 30° C. using a DMEM containing 2% horse serum.

Mouse primary myoblasts were established from mouse extensor digitorum longus muscle (EDL muscle). EDL collected from mice was placed in a DMEM GlutaMax culture medium (Thermo Fisher Scientific K.K.) containing 0.2% COLLAGENASE TYPE 1 (Worthington Biochemical Corporation), and was cultured at 37° C. for about two hours. The muscle was loosened on a 5%-BSA/PBS-coated dish (Sterilin Ltd.) with the culture medium therein, and thereby single fibers were isolated. The single fibers were cultured in 5% $CO_2$ at 37° C. using a DMEM GlutaMax culture medium containing 20% fetal bovine serum, 1% chicken embryonic extract (United States Biological Corporation), 1% penicillin/streptomycin (Wako Pure Chemical Industries, Ltd.), and 5 ng/ml bFGF (Cell Signaling Technology Inc.), and cells were liberated from the single fibers. Here, a plastic culture dish or multi-well plate (TPP Techno Plastic Products AG) coated with 1 mg/mL Matrigel (BD Biosciences) was used for the culture. Differentiation of mouse primary myoblasts into myotube cells was induced in 5% $CO_2$ at 37° C. using a DMEM GlutaMax culture medium containing 2% horse serum and 1% penicillin/streptomycin.

Human skeletal muscle satellite cells (ScienCell™ Research Laboratories Inc.) were cultured in 5% $CO_2$ at 37° C. using a Skeletal Muscle Cell Medium (ScienCell™ Research Laboratories Inc.).

Here, a plastic culture flask (Greiner Bio-One International GmbH) or multi-well plate (TPP Techno Plastic Products AG) coated with poly-L-lysine (ScienCell™ Inc.) was used for the culture.

2. Preparation of miRNA and siRNA

The miRNAs or siRNAs used in Examples were commercially available MISSION miRNA mimics (Sigma-Aldrich Co. LLC), or synthetic miRNAs or synthetic siRNAs chemically synthesized by Sigma-Aldrich Co. LLC on the basis of the information of base sequences that had been designed.

The MISSION miRNA mimics used were Negative Control (HMC0002), miR-1 (HMI0046), miR-133a (HMI0196), miR-133b (HMI0198), miR-26a (HMI0415), miR-125b (HMI0112), miR-199a-3p (HMI0338), miR-214 (HMI0379), and let-7e (HMI0013). The contents in the parentheses show product numbers.

The synthetic miRNA and siRNA having the following sequence of were used.

```
miR-199a-3p#4 s:  5'-acaguagucugcacauugguua-3':
                                                    (SEQ ID NO: 8)
miR-199a-3p#4 as: 5'-accaaugugcagacuacucauu-3':
                                                    (SEQ ID NO: 9)
siControl s:      5'-uucuccgaacgugucacguuu-3':
                                                    (SEQ ID NO: 10)
siControl as:     5'-acgugacacguucggagaauu-3':
                                                    (SEQ ID NO: 11)
siSuz12P s:       5'-acucguccaggaagaagagaauuu-3':
                                                    (SEQ ID NO: 12)
siSuz12P as:      5'-uaaauucuuucuuccuggacgagu-3':
                                                    (SEQ ID NO: 13)
siSuz12M s:       5'-gagaauuuaauggaaugauuuu-3':
                                                    (SEQ ID NO: 14)
siSuz12M as:      5'-aaucauuccauuaaauucucuu-3':
                                                    (SEQ ID NO: 15)
siLin28b#1 s:     5'-ggauucaucuccaugauaauu-3':
                                                    (SEQ ID NO: 16)
siLin28b#1 as:    5'-uuaucauggagaugaauccuu-3':
                                                    (SEQ ID NO: 17)
siLin28b#2 s:     5'-aggauuuagaagcuugaaauu-3':
                                                    (SEQ ID NO: 18)
siLin28b#2 as:    5'-uuucaagcuucuaaauccuuu-3':
                                                    (SEQ ID NO: 19)
siLin28b#3 s:     5'-guggaauuuacauuuaaaauu-3':
                                                    (SEQ ID NO: 20)
siLin28b#3 as:    5'-uuuuaaauguaaauuccacuu-3':
                                                    (SEQ ID NO: 21)
siLin28b#4 s:     5'-gagccaguggaauuuacauuu-3':
                                                    (SEQ ID NO: 22)
siLin28b#4 as:    5'-auguaaauuccacuggcucuu-3':
                                                    (SEQ ID NO: 23)
```

The sense strand (s) and antisense strand (as) that have the same name were mixed in equal amounts and annealed, and the resulting product was used in the subsequent experiments.

3. Introduction of miRNA/siRNA into Muscle Cells

Electroporation was carried out to introduce miRNA or siRNA into the cells cultured in the above-mentioned "1. Cultured Cell Line and Cell Culture".

C2C12 cells which had become 70 to 80% confluent were washed with D-PBS(−) (Wako Pure Chemical Industries, Ltd.), 0.25% Tripsin/EDTA (Sigma-Aldrich Co. LLC) was added dropwise to the cells to detach and disperse the cells, and the cells were incubated at 37° C. for three minutes. The resulting cell suspension was centrifuged at 1000×g at room temperature for three minutes, the supernatant was removed, and then $1 \times 10^6$ cells/100 μL cell suspension was prepared using Nucleaofector Solution V of an Amaxa Cell Line Nucleofector Kit V (Lonza Japan Ltd.). To 100 μL of the cell suspension, 90 pmol of MISSION miRNA mimic (Sigma-Aldrich Co. LLC) or synthetic miRNA or synthetic siRNA was added, and the resulting mixture was transferred to a cuvette attached to the Kit, followed by electroporation using a Nucleofector 2b (Lonza Japan Ltd.) (using the program of B-032) to introduce the miRNA or siRNA into the cells. After the electroporation, the cells were suspended in 500 μL of differentiation-inducible culture medium (a DMEM containing 2% horse serum) for C2C12 cells, and the resulting cells were seeded on 24-well plates at $0.2 \times 10^6$ cells per well and cultured in 5% $CO_2$ at 30° C. to bring about differentiation induction.

Mouse primary myoblasts which had become 70 to 80% confluent were washed with D-PBS(−) (Wako Pure Chemical Industries, Ltd.), 0.05% Tripsin/EDTA (Thermo Fisher Scientific K.K.) was added dropwise to the cells to detach and disperse the cells, and the cells were incubated at 37° C. for three minutes. The resulting cell suspension was centrifuged at 1800×g at room temperature for five minutes, the supernatant was removed, and miRNA or siRNA was introduced into the cells by electroporation carried out in the same manner as to the C2C12 cells. After the electroporation, the cells were suspended in 500 μL of growth culture medium (a DMEM GlutaMax culture medium containing 20% fetal bovine serum, 1% chicken embryonic extract, 1% penicillin/streptomycin, and 5 ng/mL bFGF) for mouse primary myoblasts, and the resulting cells were seeded on 24-well plates at $0.2 \times 10^6$ cells per well and cultured in 5% $CO_2$ at 30° C. to bring about differentiation induction.

Human skeletal muscle satellite cells which had become 70 to 80% confluent were washed with D-PBS(−) (Wako Pure Chemical Industries, Ltd.), 4 mL of D-PBS(−) and 1 mL of a Tripsin/EDTA solution (ScienCell Inc.) were added dropwise to the cells in culture flasks to detach and disperse the cells, and the cells were incubated at 37° C. for two minutes. The resulting cell suspension was transferred into a 15 mL Falcon tube (Thermo Fisher Scientific K.K.) with 2.5 mL of FBS (Thermo Fisher Scientific K.K.) therein, followed by incubating the flask again at 37° C. for two minutes to further disperse the remaining cells. Subsequently, 2.5 mL of Trypsin neutralization solution (ScienCell Inc.) was added dropwise, and the resulting cell suspension was transferred into the 15 mL Falcon tube. The collected cell suspension was centrifuged at 1000×g at room temperature for five minutes, the supernatant was removed, and miRNA or siRNA was introduced into the cells by electroporation carried out in the same manner as to the C2C12 cells. After the electroporation, the cells were suspended in 500 μL of growth culture medium (Skeletal Muscle Cell Medium) for human skeletal muscle satellite cells, and the resulting cells were seeded on 24-well plates at $0.2 \times 10^6$ cells per well and cultured in 5% $CO_2$ at 37° C.

4. Muscle Injury to Mouse Anterior Tibial Muscle and Intramuscular Injection of miRNA Eight- to nine-week-old male mice, C57BL/6J (Charles River Laboratories Japan, Inc.), or naturally aged ICR mice (CLEA Japan, Inc.) that had grown for two or more years after birth were used as experimental animals.

Muscle injury was caused to mice by intramuscularly injecting 50 μL of 1.2% (w/v) barium chloride ($BaCl_2$) (Wako Pure Chemical Industries, Ltd.) solution into the anterior tibial muscle of the left hindlimb of mice using a 1 mL syringe with a 26 gauge needle (Terumo Corporation). RNA was administered to the injured site by intramuscularly injecting 50 μL of a solution mixture into the injured site of each mouse on the day after injury to the muscle (with barium chloride administered), wherein the solution mixture was prepared by mixing AtelloGene (registered trademark) and 10 μM miR-199a-3p mimic or siControl (control RNA)

in equal amounts using an AteloGene (registered trademark) Local Use (KOKEN Co., Ltd.) kit.

5. Staining of Muscle Tissue

Anterior tibial muscle was enucleated from mice on Day 10 after injury to the muscle, and the anterior tibial muscle was quickly frozen in isopentane (Wako Pure Chemical Industries, Ltd.) cooled with liquid nitrogen. A 10 µm thick frozen transverse section of anterior tibial muscle was made using a cryostat CM1900 (Leica Microsystems K.K.), and underwent HE staining. The stained muscle tissue was observed using an Axiovert 40 CFL (Carl Zeiss AG) and the Axiovision Rel 4.6 software (Carl Zeiss AG). Using the ImageJ software, the cross-sectional area of muscle fibers having the central nucleus was measured, wherein the cross-sectional area is an index of the muscle regenerated from the injury. A cross-sectional area having at least 700 muscle fibers (at least 100 muscle fibers in the case of old mice) was measured per individual mouse. The siControl and the miR-199a-3p mimic treated group were tested by student's t-test for statistically significant difference between them.

6. Total RNA Extraction and RT-qPCR Analysis

Total RNA derived from cells and from the anterior tibial muscle on Day 3 after the muscle injury was extracted using a TRI Reagent (Molecular Research Center, Inc.). cDNA was synthesized from mRNAs in the total RNA using Oligo $dT_{15}$ primer (Promega Corporation) as a primer for cDNA synthesis and SuperScript III (Thermo Fisher Scientific K.K.) as a reverse transcriptase in accordance with the attached protocols. Using the synthesized cDNA, a Fast SYBR Green Master Mix (Roche Molecular Systems, Inc.), and Perfect Real Time primers (TAKARA Bio Inc.) for the genes of interest, qPCR (quantitative PCR) analysis was carried out with a StepOne Plus Real-Time PCR system (Thermo Fisher Scientific K.K.). The obtained data were analyzed by Comparative CT method (ΔΔCT method) using, as an endogenous standard gene, the Gapdh gene and the Actb gene for culture cells and muscle tissue samples, respectively. Thereby, the relative expression level was calculated.

As primers, primer pairs, Myog (MA127738), Myh1 (MA149010), MyoD (MA128901), Gapdh (MA050371), Myh4 (MA116815), Myf5 (MA075089), Mef2c (MA107825), Ckm (MA112761), Actb (MA050368), MEF2C (HA103691), MYH4 (HA155834), and GAPDH (HA067812) from TAKARA BIO Inc. were used. The letters and numbers in the parentheses accompanying the primer set names show the product numbers of TAKARA BIO Inc.

To examine the expression level of mature miRNA in the muscle-differentiation-related miRNA, cDNA was also synthesized using TaqMan (registered trademark) MicroRNA Assays (Thermo Fisher Scientific K.K.) and a TaqMan MicroRNA Reverse Transcription Kit (Thermo Fisher Scientific K.K.) in accordance with the attached protocols. The synthesized cDNA was subjected to qPCR analysis using a TaqMan Fast Advanced Master Mix (Thermo Fisher Scientific K.K.), TaqMan MicroRNA Assays (Thermo scientific K.K.), and a StepOne Plus Real-Time PCR system (Thermo Fisher Scientific K.K.) in accordance with the attached protocols. The data were normalized by ΔΔCt method using an internal standard gene to measure the expression level.

The muscle-differentiation-related miRNAs used in the TaqMan MicroRNA assay were miR-1a-3p (2222), miR-133a-3p (2246), miR-214-3p (2306), miR-26a-5p (405), let-7g (2282), and miR-199a-3p (2304) from Thermo Fisher Scientific K.K., and U6 snRNA (1973) was used as an internal standard gene. The numbers in the parentheses accompanying the miRNA names show the product numbers of Thermo Fisher Scientific K.K.

7. Western Blot Analysis

Cell extract was prepared using a RIPA Lysis and Extraction buffer (Thermo Fisher Scientific K.K.) containing a protease inhibitor (Complete Mini; Roche Molecular Systems, Inc.). Proteins in the cell extracts were electrophoretically separated according to the molecular weight on SDS-polyacrylamide gels (SDS-PAGE), and then the proteins on the gels were transferred electrophoretically onto PVDF membranes (Merck Millipore). Subsequently, after the transfer, the membranes were blocked using TBS (20 mM Tris, 500 mM NaCl, pH7.5) containing 5% skim milk (Wako Pure Chemical Industries, Ltd.) and 0.1% Tween 20 (Nacalai Tesque, Inc.). The blocked membranes were dipped in a primary antibody liquid diluted with TBS containing 5% BSA (Sigma-Aldrich Co. LLC) (or 1% skim milk) and 0.1% Tween 20, and shaked at 4° C. overnight. Anti-Suz12 (#3737, 1000-fold diluted, Cell Signaling Technology Japan, K.K.), Anti-Lin28b (#5422, 1000-fold diluted, Cell Signaling Technology Japan, K.K.), Anti-Myosin heavy chain (MF20) (#MAB4470, 200-fold diluted, R&D Systems, Inc.), and Anti-α-Tubulin (#F2168, 5000-fold diluted, Sigma-Aldrich Co. LLC) were used as the primary antibodies. After washing the membranes, secondary antibody reaction was carried at room temperature for 30 minutes using HRP-labeled goat antimouse IgG (or HRP-labeled goat antirabbit IgG) (Sigma-Aldrich Co. LLC) diluted 5000-fold with TBS containing 1% skim milk and 0.1% Tween 20. The membranes were washed again, and then were subjected to a luminescent reaction using an ECL Prime Western Blotting Detection Reagent (GE Healthcare Japan Corporation), and light exposure and band detection were carried out using a LAS500 (GE Healthcare Japan Corporation).

Example 1: Induction of Muscle Differentiation by miR-199a-3p in Mouse Myoblast (Purpose)

The Induction activity of muscle differentiation by the miR-199a-3p constituting the inducer of muscle differentiation according to the present invention to the myoblasts is verified.

(Method and Results)

Each of the miRNAs, i.e. miR-199a-3p, miR-1, miR-133a, miR-26a, miR-214, miR-125a, miR-133b, and Let-7e was introduced by electroporation into mouse myoblast line C2C12 cells, the resulting cells were seeded in a culture medium (2% HS/DMEM) for muscle differentiation and cultured at 30° C. for three days, and the total RNA of the cultured cells was used to verify the expression levels of muscle differentiation marker proteins, Myogenin (Myog) and Myh1, by RT-qPCR.

The results are shown in FIG. 1. "A" and "B" show the expression levels of Myog and Myh1, respectively. In both cases of the markers, C2C12 cells with miR-199a-3p introduced thereinto exhibited a remarkably higher expression level of muscle differentiation marker than C2C12 cells with other miRNAs introduced thereinto. These results suggest that the miR-199a-3p has a higher induction activity of the differentiation for myoblasts.

Example 2: Expression Level of Muscle-Differentiation-Related miRNA with miR-199a-3p (Purpose)

The expression levels of muscle-differentiation-related miRNA in C2C12 cells after introducing miR-199a-3p constituting the inducer of muscle differentiation according to the present invention are verified.

(Method and Results)

The expression levels of miR-1, miR-133a, miR-26a, let-7g, and miR-214 in C2C12 cells after introducing miR-199a-3p were measured by ΔΔCt method analysis using U6 snRNA as an internal standard gene. As the miR-199a-3p to be introduced, miR-199a-3p (HMI0338: a MISSION miRNA mimic) (referred to as "199s" for short) and miR-199a-3p#4 (referred to as "199#4#" for short) were used.

Figures 1, 2:
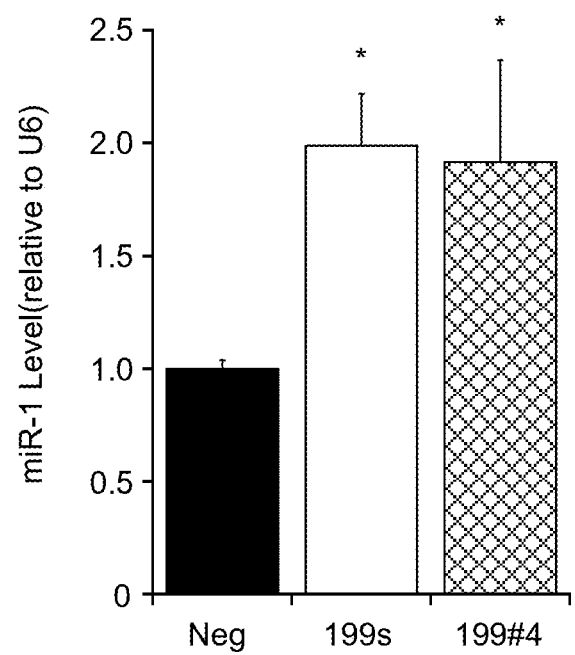
Figure 2:
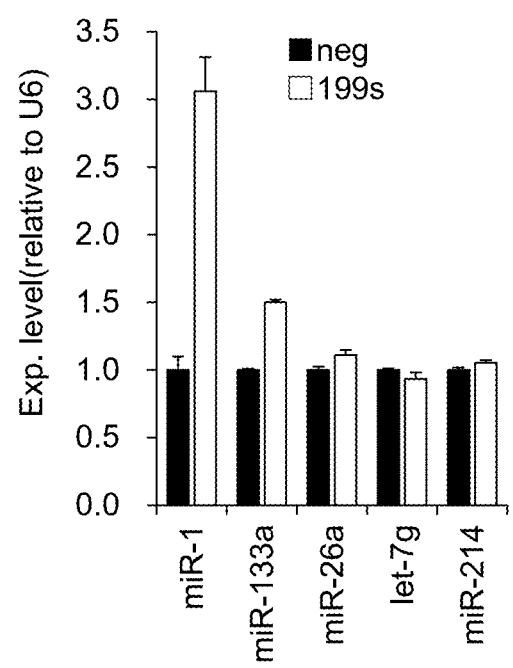

The results are shown in FIG. 2. As shown in FIG. 2-1, the expression levels of miR-1 with 199s and 199#4 were significantly higher than the control (neg). In addition, FIG. 2-2 shows that, in C2C12 cells with 199s introduced thereinto, the expression of miR-1 and miR-133a was remarkably increased, compared with the control (neg). These results suggest that miR-199a-3p functions superiorly to miR-1 in muscle differentiation.

Example 3: Suppression of Expression of Target Candidate Gene by miR-199a-3p (Purpose)

Figures 1, 3:
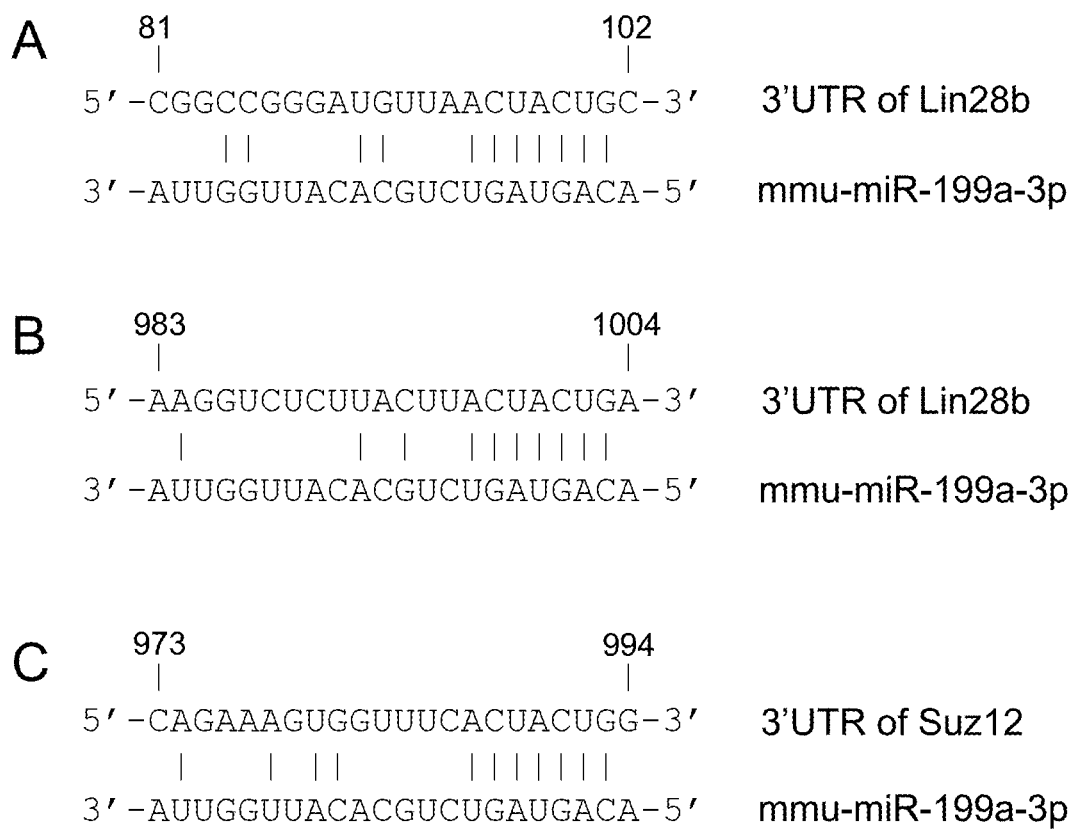
Figures 2, 3:
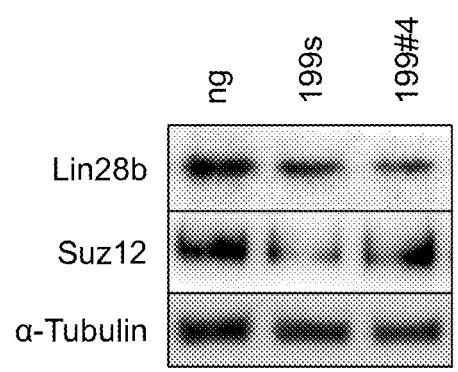

From the base sequence shown in miR-199a-3p, the Lin28b gene and Suz12 gene were deduced as target candidate genes of miR-199a-3p. As shown in FIG. 3-1, the mouse miR-199a-3p has two candidate target sites (A: positions 81 to 102, and B: positions 983 to 1004) on the Lin28b gene and one candidate target site (C: positions 973 to 994) on the Suz12 gene. In view of this, verification was carried out to see whether the expression of the target candidate genes, Lin28b gene and Suz12 gene, was suppressed in C2C12 cells when miR-199a-3p was introduced into the cells.

(Method and Results)

miR-199a-3p was introduced into C2C12 cells, and the resulting cells were cultured and then prepared into a cell extraction liquid in accordance with a conventional method. The cell extraction liquid was subjected to Western blotting, whereby the expression levels of the Lin28b protein and Suz12 protein were detected using the respective antibodies for the proteins.

The results are shown in FIG. 3-2. Introduction of miR-199a-3p (199s and 199#4) exhibited a reduction in the amounts of the Lin28b and Suz12 proteins, compared with the control (ng). These results suggest that the target genes of miR-199a-3p are the Lin28b gene and Suz12 gene.

Example 4: Relationship Between Target Gene of miR-199a-3p and Muscle-Differentiation-Related Gene (Purpose)

The expression levels of muscle-differentiation-related genes based on the expression suppression of Lin28b and Suz12 that were the target genes of miR-199a-3p are verified.

(Method and Results)

For expression suppression of Lin28b and Suz12, the respective siRNAs against them were used. The muscle-differentiation-related genes were Myog, Myh1, and Ckm. Each siRNA was introduced into C2C12 cells, the resulting cell was seeded in a culture medium for muscle differentiation and cultured at 30° C. for three days, and the total RNA extracted from the cells was examined by RT-qPCR.

Figures 1, 4:
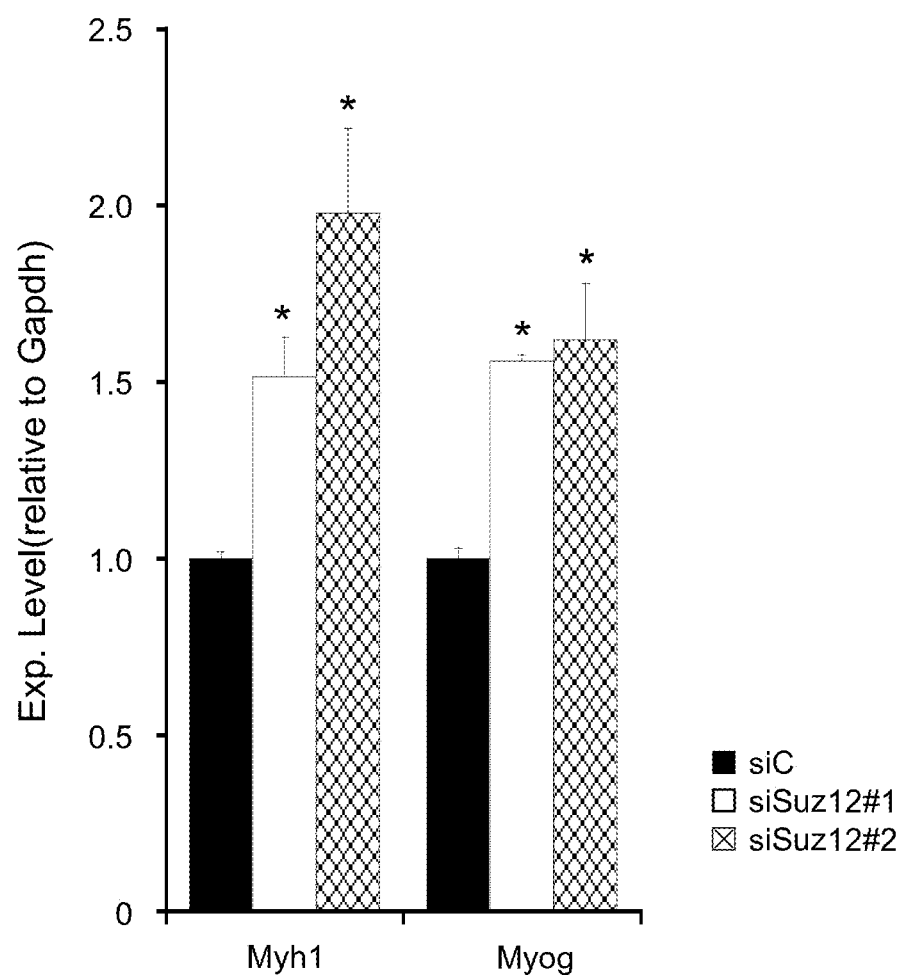
Figures 2, 4:
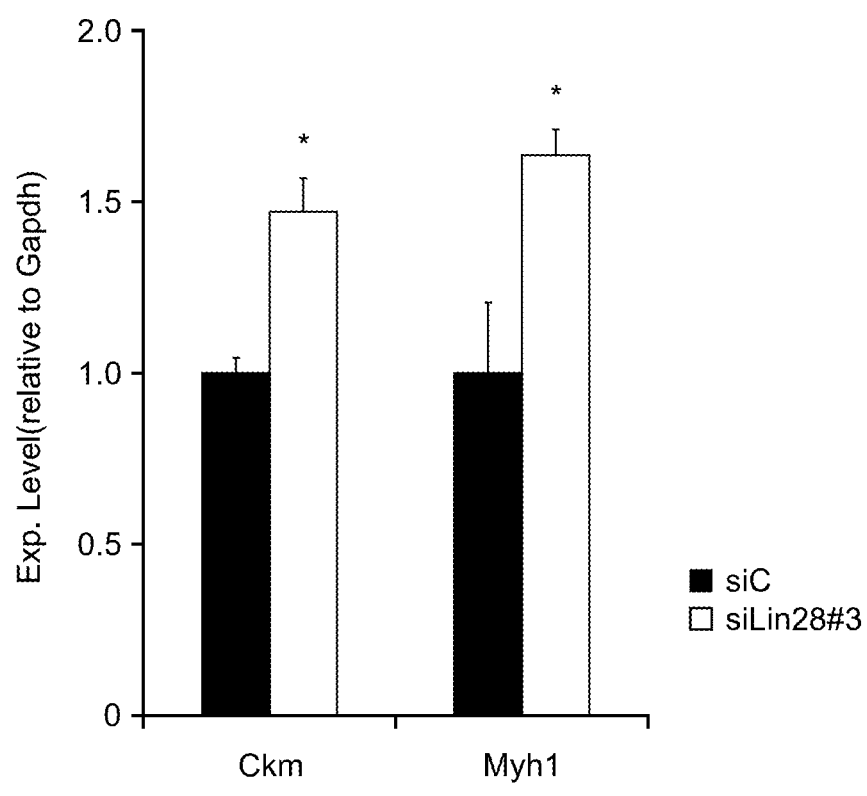

The results are shown in FIG. 4. FIG. 4-1 shows the expression levels of Myh1 and Myog in the presence of siRNA (siSuz12#1 and siSuz12#2) against Suz12, and FIG. 4-2 shows the expression levels of Ckm and Myh1 in the presence of siRNA (siLin28#3) against Lin28b.

As seen in FIG. 4-1, the expression levels of Myh1 and Myog significantly increased owing to the Suz12 expression suppressed by siSuz12#1 or siSuz12#2. Also as seen in FIG. 4-2, the expression levels of Ckm and Myh1 significantly increased owing to the Lin28b expression suppressed by siLin28#3.

The above-mentioned results suggest that Lin28b and Suz12 regulate muscle differentiation suppressively and that this suppression is removed by suppressing the expression of Lin28b and Suz12. In other words, the results have suggested that miR-199a-3p can induce muscle differentiation via suppression of the expression of Lin28b and Suz12 which are target genes.

Example 5: Muscle Differentiation Induction by Introduction of miR-199a-3p into Mouse Primary Myoblast (Purpose)

Verification is carried out about whether the same effects as obtained from the mouse myoblast line C2C12 cells are obtained from the primary cultured cells derived from mouse extensor digitorum longus muscle when miR-199a-3p is introduced.

(Method and Results)

Primary culture cells were prepared from two mice, the cells were equally divided into three portions, one for ng, another for 199s, and the other for 199#4, which were regarded as a culture group for one time, and the procedure was independently carried out four times (c5 to c8). In to the cells, 199s or 199#4 as miR-199a-3p was introduced, and the cells were cultured in a growth culture medium for two days and underwent differentiation induction. RNA was collected from the cells one day after differentiation induction, and the expression level of miR-1 and the expression levels of muscle differentiation markers, Ckm, Myog, Mef2c, and Myh4, were measured by RT-qPCR.

Figures 1, 5:
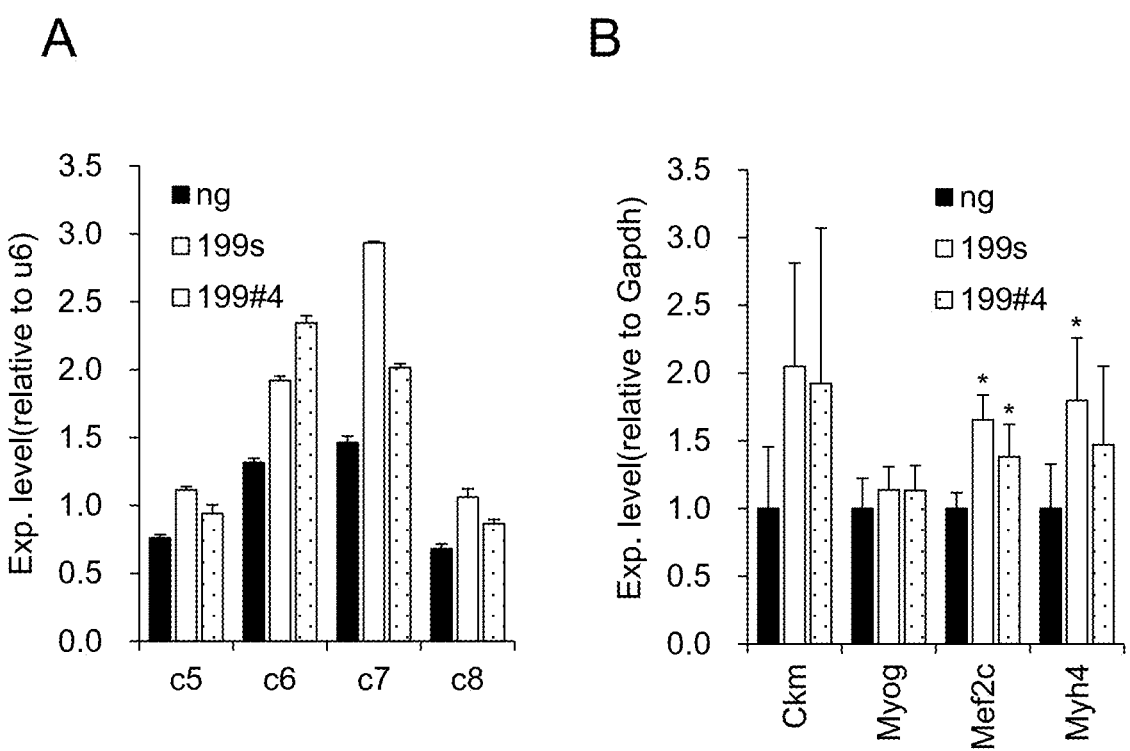
FIG. 5 (A-B) is a diagram showing the induction activity of muscle differentiation when miR-199a-3p was introduced into the primary cultured cells derived from mouse extensor digitorum longus muscle. "A" shows the expression level of miR-1 in the primary cultured cells (c5 to c8) introducing miR-199a-3p (each of 199s and 199#4). "B" shows the average value of the expression levels of Ckm, Myog, Mef2c, and Myh4 in c5 to c8.
Figures 2, 5:
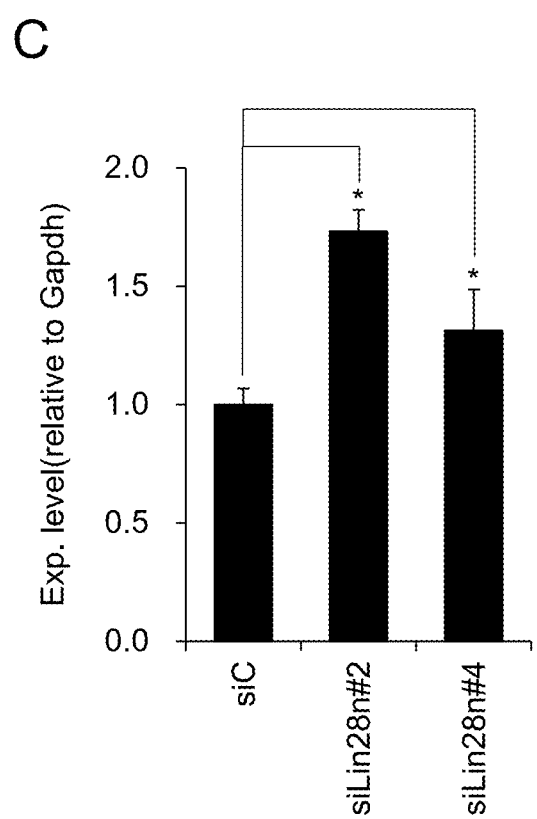

The results are shown in FIG. 5. A in FIG. 5-1 shows the results obtained from measuring, by RT-qPCR, the expression level of miR-1 in each group of the primary cultured cells into which miR-199a-3p (199s and 199#4) was introduced. The primary culture cells were very unstable, and accordingly, even in the same experiment, different culture groups prepared exhibited different expression levels, but all culture groups showed a similar expression pattern. In addition, B in FIG. 5-1 shows the average value of the expression levels of Ckm, Myog, Mef2c, and Myh4 in each group. Furthermore, C in FIG. 5-2 shows the results obtained from measuring, by RT-qPCR, the expression level of Ckm in the presence of siLin28b.

Example 6: In Vivo Induction of Muscle Differentiation by miR-199a-3p (Purpose)

The induction of muscle differentiation is verified when the miR-199a-3p constituting the inducer of muscle differentiation according to the present invention was introduced into muscle injured-mice.

(Method and Results)

The anterior tibial muscle (TA muscle) of eight-week-old C57/BL6J mice was injured by administration of $BaCl_2$. After 24 hours, miR-199a-3p was administered to the same site. After further 48 hours, the TA muscle was enucleated, and, using the total RNA, RT-qPCR analysis was carried out to examine the expression of the muscle differentiation markers, Myog, Myod1, and Myf5.

Figure 6:
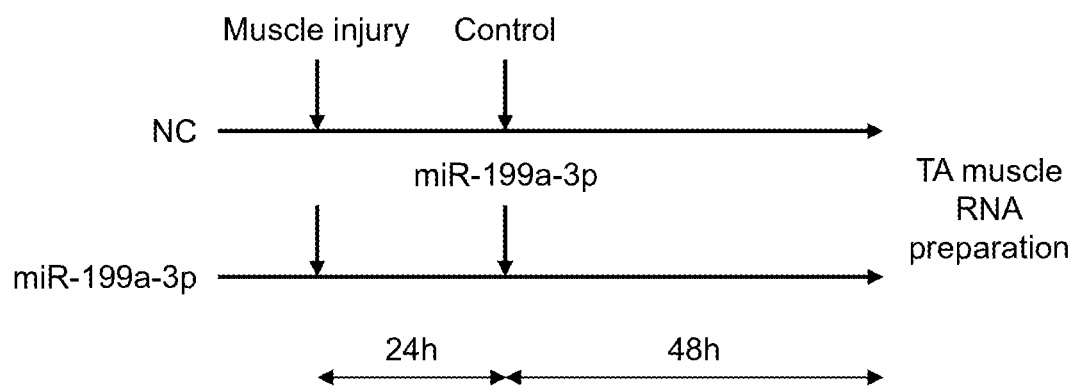
FIG. 6 (A-B) is a diagram showing the results of in vivo induction of muscle differentiation under the presence of miR-199a-3p. "A" shows the experiment schedule of Example 6. "B" shows the expression level of each muscle differentiation marker. In the diagram, NC represents a negative control.
Figure 6:
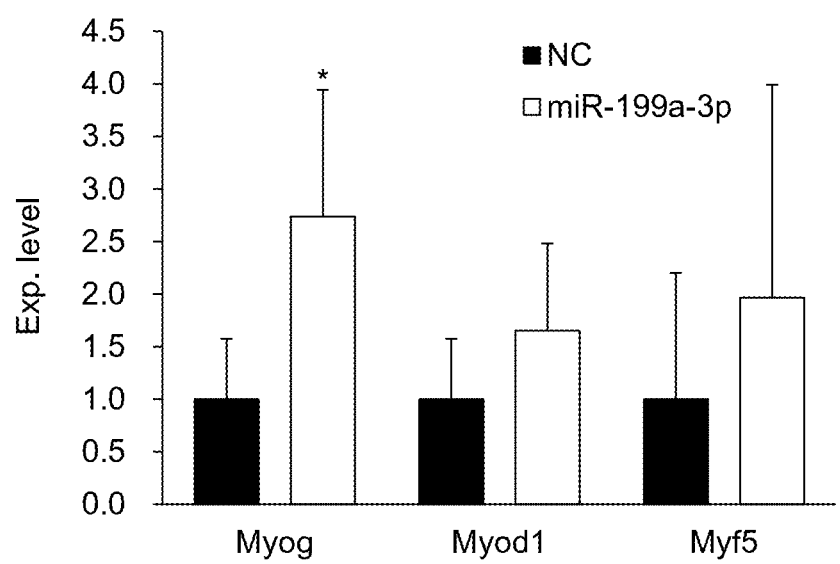

The results are shown in FIG. 6. "A" shows the experiment schedule of the present Example. "B" shows the expression level of each muscle differentiation marker. Introduction of miR-199a-3p significantly increased the expression of Myog (n=8), compared with the control (NC). This result has revealed that miR-199a-3p has an induction activity of muscle differentiation also in vivo. There was no recognized significant difference in expression between Myf5 and Myod1, and this is considered to be due to a difference in timing of expression between Myog and Myf5 or Myod1. It is generally known that, in the muscle differentiation, the expression of Myf5 or Myod1 is activated, after skeletal muscle satellite cells in a resting state turn into activated skeletal muscle satellite cells by stimulation. By contrast, the expression of Myog is activated, after myoblasts enter into the differentiation state for myotube cells. In this embodiment, the experiment was carried out in the timing of expression of Myog, and this is inferred because the expression of Myf5 and Myod1 was not sufficiently activated, the significant difference was not shown. However, it is obvious from "B" in FIG. 6 that the expression levels of Myf5 and Myod1 tend to increase in the cells introduced miR-199a-3p

Example 7: In Vivo Promotion Activity of Muscle Regeneration with miR-199a-3p (Purpose)

Verification is carried out to show that miR-199a-3p also has a promotion activity of muscle regeneration for old mice.

(Method and Results)

The anterior tibial muscles (TA muscles) of eight-week-old C57/BL6J mice and two-year-old ICR mice were injured by administration of $BaCl_2$. After 24 hours, miR-199a-3p was administered to the same site. After further nine days, frozen sections of the TA muscle were prepared, and the cross-sectional area of the muscle fibers during regeneration was measured by HE staining. The muscle fibers during regeneration have a nucleus in the center, and the nucleus was used as a mark in counting. The number of muscle fibers measured per individual was more than 700 fibers in eight-week-old mice and more than 100 fibers in two-year-old mice.

Figure 7:
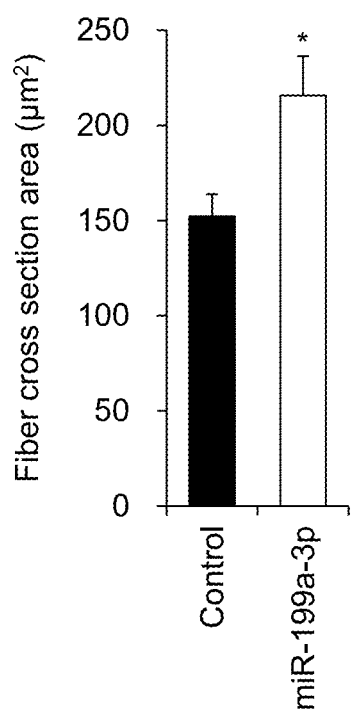
Figure 2:
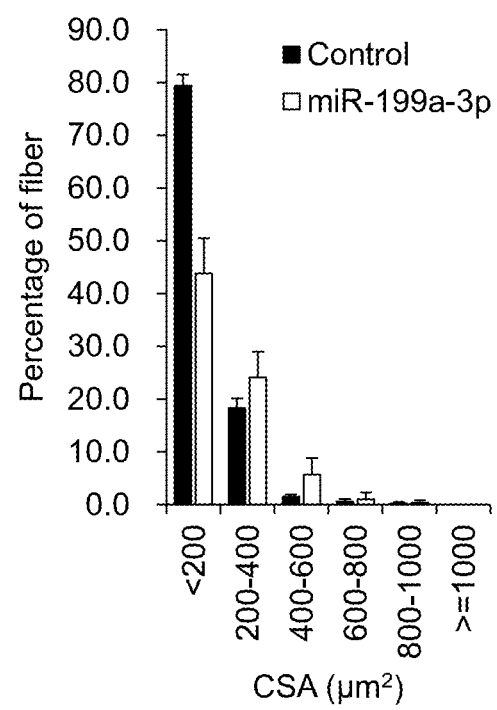

The results are shown in FIG. 7. In FIG. 7-1, "A" shows the experiment schedule of the present Example. "B" and "C" show the results from the eight-week-old C57/BL6J mice, and "D" and "E" in FIG. 7-2 show the results from the two-year-old ICR mice.

"B" and "D" show the average values of the muscle fiber cross-sectional areas of the anterior tibial muscles under the course of regeneration (n=3). "C" and "E" each show the number of muscle fibers in each muscle fiber cross-sectional area (n=3). The results have revealed that administration of miR-199a-3p after muscle injury to eight-week-old mice and two-year-old mice allowed the both types of mice to have a significantly ager muscle fiber cross-sectional area and promoted muscle regeneration. In addition, the fact that even the two-year old mice underwent muscle regeneration to the same degree as the eight-week-old mice suggests that miR-199a-3p constituting the inducer of muscle differentiation according to the present invention is effective also for old individuals.

Example 8: Induction of Muscle Differentiation by Introduction of miR-199a-3p into Human Skeletal Muscle Satellite Cell (Purpose)

Verification is carried out to see that the same effects as obtained from the mouse myoblast lines are obtained also from the human skeletal muscle satellite cells introduced miR-199a-3p.

(Method and Results)

miR-199a-3p was introduced into human skeletal muscle satellite cells, the cells were cultured in a growth culture medium for three days, RNA was collected from the cells, and the expression of muscle differentiation marker, MEF2C and MYH4, was examined by RT-qPCR.

Figure 8:
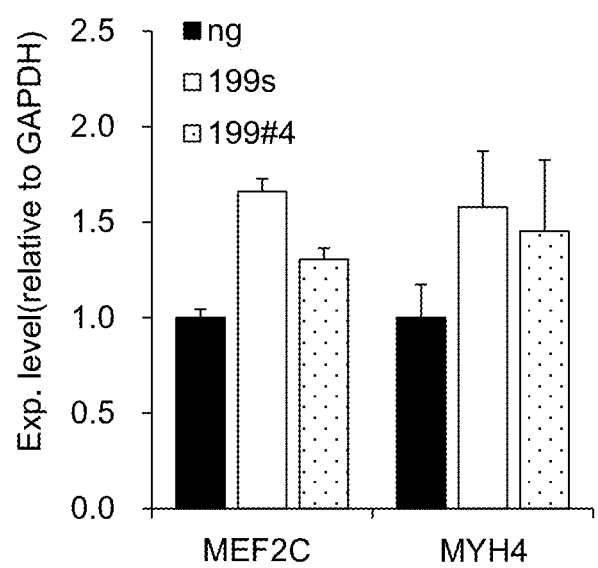
FIG. 8 is a diagram showing the induction of muscle differentiation brought by introduction of miR-199a-3p to human skeletal muscle satellite cells.

The results are shown in FIG. 8. The results have demonstrated that, also in a case of the human skeletal muscle satellite cells having miR-199a-3p, the miR-199a-3p (199s and 199#4) can induce muscle differentiation in the same manner as in the cases of mouse myoblast lines and primary myoblasts.

Example 9: Improvement in Muscle Strength of mdx Mouse by Administration of miR-199a-3p (Purpose)

Improvement in the muscle strength of muscular dystrophy model mice (mdx mice) administering miR-199a-3p is verified by grip test.

(Method and Results)

The 199#4 as miR-199a-3p and the siControl as a control were each administered to the tail veins of seven-week old male mdx mice and brood male normal mice (B10) at a dose of 1.6 µg/Kg B.W. per mouse using an AteloGene (registered trademark) Systemic Use (KOKEN Co., Ltd.) kit.

One week after the introduction, the grip strength of the mice was measured by grip test using a small animal grip strength measurement device (GPM-100B, Melquest Ltd.). Specifically, each mouse was allowed to grip the measurement bar with its forefeet, the tail of the mouse was pulled such that the mouse is postured horizontally, and a value just before the mouse released its forefeet from the measurement bar was obtained as a grip strength value. The number of mice in the test groups used for the grip test were: 11 mice in the group of normal mice B10 administering siControl (B10-siC); 11 mice in the group of normal mice B10 administering 199#4 (B10-199#4); 9 mice in the group of mdx mice administering siControl (mdx-siC); and 10 mice in the group of mdx mice administering 199#4 (mdx-199#4).

Figure 9:
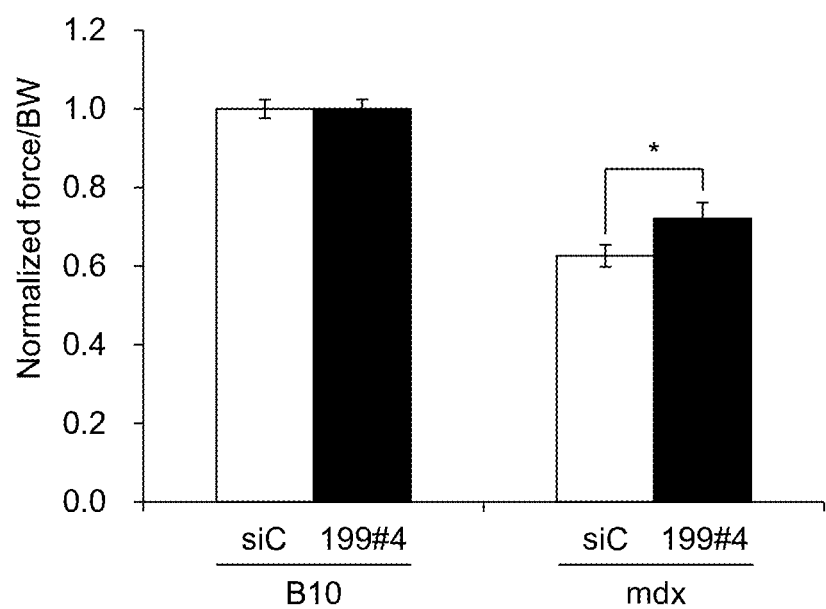
FIG. 9 shows the results of grip tests by normal mice (B10) and muscular dystrophy model mice (mdx) administering miR-199a-3p or siControl as a control. In the diagram, siC and 199#4 represent siControl and miR-199a-3p, respectively.

The results are shown in FIG. 9. This diagram shows the relative value of each of the mdx mice groups (mdx-siC and mdx-199#4) assuming that the measurement values in the normal mice groups (B10-siC and B10-199#4) are each 1.

The mdx-siC group and mdx-199#4 group presenting a muscular dystrophy-like symptom had only 60 to 70% basic grip strength, compared with the normal mice B10 group. However, the results have revealed that the grip strength of the mdx-199#4 group administering 199#4 to mdx mice was significantly enhanced, though the group were also mdx mice, compared with the mdx-siC group for a control. These results have demonstrated that administration of miR-199a-3p enhances muscle strength and suggests that miR-199a-3p is capable of becoming an active ingredient of a muscular dystrophy treatment agent.

Example 10: Verification of Level of Muscle-Specific miRNAs in the Blood of mdx Mice with miR-199a-3p Administered Thereto (Purpose)

It is known that muscular dystrophy patients and mdx mice have statistically significantly increased amounts of three muscle-specific miRNAs (miR-1, miR-133a, and miR-206) in serum, compared with healthy subjects and normal mice (Matsuzaka Y, et al., PLoS One. 2016 Dec. 15; 11(12):e0167811). In view of this, the improvement of these miRNAs in the blood of mdx mice whose muscle strength was recovered by administering miR-199a-3p is verified.

(Method and Results)

After measuring muscle strength of each mouse administering miR-199a-3p in Example 9, the blood from heart of each mouse was collected using an anti-coagulant, EDTA. Furthermore, blood plasma was obtained from the collected whole blood using a conventional method. Subsequently, RNA was extracted from 200 µL of the blood plasma of each mouse using a plasma/serum circulating and exosomal RNA purification mini kit (Norgen Biotek Corp.) in accordance with the attached protocols. During the RNA extraction, cel-miR-39 was added as an external standard gene.

Two kinds of muscle-specific miRNAs (miR-1 and miR-133a) were subjected to RT-qPCR using a TaqMan assay (Thermo Fisher Scientific K.K.) and a FastStart Universal Probe Master (Rox) (Roche Molecular Systems, Inc.). Subsequently, the data was analyzed by ΔΔCt method analysis using cel-miR-39 and B10-siC as internal standard genes, and then statistical analysis by Welch's t-test was carried out.

Figure 10:
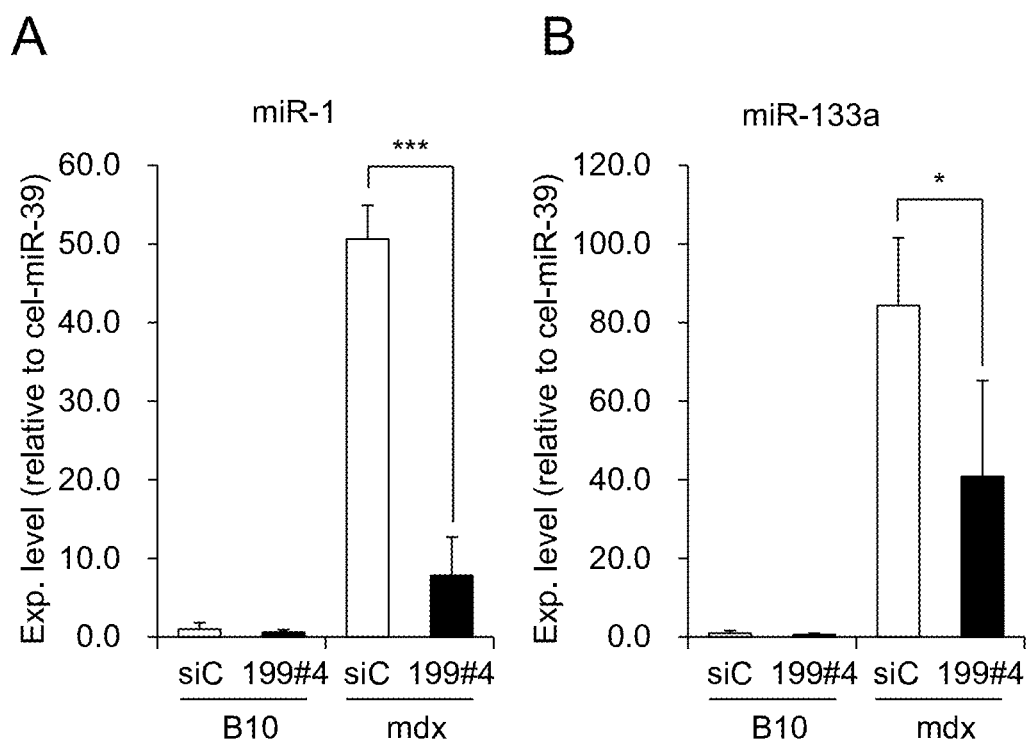
FIG. 10 (A-B) shows the amounts of muscle-specific miRNAs (miR-1 and miR-133a) in the blood plasma of normal mice (B10) and muscular dystrophy model mice (mdx) administering miR-199a-3p or siControl as a control. "A" and "B" show the expression levels of miR-1 and miR-133a, respectively, in the blood plasma. In the diagram, siC and 199#4 represent siControl and miR-199a-3p, respectively.

The results are shown in FIG. 10. As the amounts of miR-1(A) and miR-133a(B) in the blood plasma, the normal mouse groups (B10-siC and B10-199#4) exhibited low values, but the mdx mice group (mdx-siC) into which siControl for a control was introduced exhibited remarkably high values in the same manner as the findings with conventional serum. However, the results have revealed that the amounts of both miR-1 and miR-133a in the blood plasma were statistically significantly decreased in the mdx mice group (mdx-199#4) with 199#4 introduced therein as miR-199a-3p, compared with mdx-siC. These results biochemically support the recovery of mdx mice's muscle strength by miR-199a-3p and suggest that miR-199a-3p has an effect for the recovery of muscle strength and suppression of the amount of muscle-specific miRNAs in the blood of muscular dystrophy patients.

Example 11: Verification of CK Activity in the Blood of mdx Mouse with miR-199a-3p Administered Thereto (Purpose)

Muscular dystrophy patients undergo the degeneration or necrosis of the muscle fibers of the skeletal muscle, whereby creatine kinase contained in muscle cells leak out into the blood. Therefore, it is known that value of creatine kinase activity (CK activity) in the blood is statistically significantly high in the muscular dystrophy patients, compared with that in healthy subjects (Allen D. G., et al., 2016, Physiol Rev. January; 96(1):253-305). In view of this, the blood CK activity in mdx mice administering miR-199a-3p is verified.

(Method and Results)

Plasma CK activity in the blood was measured using the blood plasma collected in Example 10 and using a Creatine Kinase Activity Assay Kit (Colorimetric) (Abcam plc.) in accordance with the attached protocols. A SYNERGY H1 microplate reader (BioTek Instruments, Inc.) was used as a measurement device, Gen5 2.07 was used as the analysis software, and, after analyzing the data, statistical test by Welch's t-test was carried out.

Figure 11:
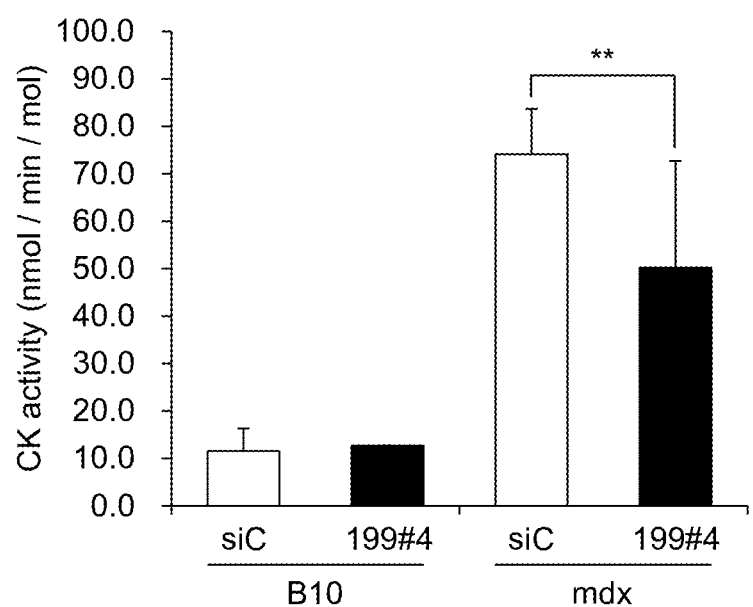
FIG. 11 shows the creatine kinase (CK) activity in the blood plasma of normal mice (B10) and muscular dystrophy model mice (mdx) administering miR-199a-3p or siControl as a control. In the diagram, siC and 199#4 represent siControl and miR-199a-3p, respectively.

The results are shown in FIG. 11. As the CK activity in the blood plasma, the normal mouse groups (B10-siC and B10-199#4) exhibited low values, but the mdx mice group (mdx-siC) introduced with siControl as a control exhibited high values. This shows that, as with muscular dystrophy patients, mdx-siC was such that skeletal muscle damage caused creatine kinase in muscle cells to leak out into the blood. Unlike this, the results have revealed that the CK activity in the blood plasma was statistically significantly decreased in the mdx mice group (mdx-199#4) with 199#4 administered thereto as miR-199a-3p, compared with mdx-siC. This result suggests that miR-199a-3p also has an effect for the suppression of the CK activity in blood in muscular dystrophy patients. At the same time, the result also suggests that miR-199a-3p can be an active ingredient which suppresses the degeneration and necrosis of muscle cells of muscular dystrophy patients.

All publications, patents, and patent applications cited herein are incorporated herein by reference in their entirety.

The invention claimed is:

1. A method for treating a disorder or a disease associated with muscle atrophy or muscle injury, comprising, administering an inducer of skeletal muscle differentiation to a subject in need thereof,
wherein the inducer of skeletal muscle differentiation consists of a synthetic miR-199 consisting of polynucleotides having base sequences of SEQ ID NOs: 8 and 9 or DNA containing a synthetic miR-199 gene encoding the synthetic miR-199.

2. The method according to claim 1, wherein the myogenic disease is muscular dystrophy.

3. A method for treating a disorder or a disease associated with muscle atrophy or muscle injury, comprising,
administering an inducer of skeletal muscle differentiation to a subject in need thereof,
wherein the inducer of skeletal muscle differentiation consists of an miR-199 or a DNA containing an miR-199 gene encoding the miR-199, wherein the disease associated with muscle atrophy or muscle injury is a myogenic disease.

4. The method according to claim 3, wherein the myogenic disease is muscular dystrophy.

* * * * *